(12) United States Patent
Treace et al.

(10) Patent No.: US 11,890,039 B1
(45) Date of Patent: Feb. 6, 2024

(54) MULTI-DIAMETER K-WIRE FOR ORTHOPEDIC APPLICATIONS

(71) Applicant: Treace Medical Concepts, Inc., Ponte Vedra, FL (US)

(72) Inventors: John T. Treace, Ponte Vedra Beach, FL (US); Sean F. Scanlan, Jacksonville, FL (US); Michael Stedham, Jacksonville, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 525 days.

(21) Appl. No.: 17/018,422

(22) Filed: Sep. 11, 2020

Related U.S. Application Data

(60) Provisional application No. 62/900,391, filed on Sep. 13, 2019.

(51) Int. Cl.
    *A61B 17/72*     (2006.01)
    *A61B 17/84*     (2006.01)
    *A61B 17/88*     (2006.01)

(52) U.S. Cl.
    CPC ........ *A61B 17/7291* (2013.01); *A61B 17/848* (2013.01); *A61B 17/8875* (2013.01)

(58) Field of Classification Search
    CPC .............. A61B 17/7291; A61B 17/848; A61B 2017/565; A61B 17/846; A61B 17/8897
    See application file for complete search history.

(56) References Cited

U.S. PATENT DOCUMENTS

| | | |
|---|---|---|
| 3,664,022 A | 5/1972 | Small |
| 4,069,824 A | 1/1978 | Weinstock |
| 4,159,716 A | 7/1979 | Borchers |

(Continued)

FOREIGN PATENT DOCUMENTS

| | | |
|---|---|---|
| AU | 2006252612 B2 | 4/2012 |
| AU | 2009227957 B2 | 7/2014 |

(Continued)

OTHER PUBLICATIONS

Nagy et al., "The AO Ulnar Shortening Osteotomy System Indications and Surgical Technique," Journal of Wrist Surgery, vol. 3, No. 2, 2014, pp. 91-97.

(Continued)

*Primary Examiner* — Julianna N Harvey
(74) *Attorney, Agent, or Firm* — Fredrikson & Byron, P.A.

(57) ABSTRACT

A multi-diameter fixation pin, such as a K-wire can be used during an orthopedic procedure. The multi-diameter fixation pin may include a leading diameter sized for the specific orthopedic procedure being undertaken and/or the size of the bone into which the fixation pin is being inserted. The multi-diameter fixation pin may include a trailing diameter different than the leading diameter. The trailing diameter may be sized for use with a specific sized powered driver. For example, in orthopedic procedures that involve inserting larger diameter pins and smaller diameter pins into bone(s), all pins used in the procedure may have a trailing diameter (e.g., the larger diameter or the smaller diameter) that allows the pins to be inserted with the same powered driver (e.g., the same attachment head) without needing different sized drivers or attachment heads for different sized pins.

20 Claims, 15 Drawing Sheets

(56) References Cited

U.S. PATENT DOCUMENTS

| | | |
|---|---|---|
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,895,141 A | 1/1990 | Koeneman et al. |
| 4,952,214 A | 8/1990 | Comparetto |
| 4,959,065 A | 9/1990 | Arnett et al. |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,304,180 A | 4/1994 | Slocum |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,413,579 A | 5/1995 | Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| 5,690,639 A | 11/1997 | Lederer et al. |
| 5,702,396 A | 12/1997 | Hoenig et al. |
| H1706 H | 1/1998 | Mason |
| 5,709,686 A | 1/1998 | Talos et al. |
| 5,709,687 A | 1/1998 | Pennig |
| 5,722,978 A | 3/1998 | Jenkins |
| 5,749,875 A | 5/1998 | Puddu |
| 5,779,709 A | 7/1998 | Harris et al. |
| 5,785,712 A | 7/1998 | Runciman et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | McGuire |
| 6,030,391 A | 2/2000 | Brainard et al. |
| 6,110,174 A * | 8/2000 | Nichter .......... A61B 17/8872 606/103 |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,478,799 B1 | 11/2002 | Williamson |
| 6,511,481 B2 | 1/2003 | von Hoffmann et al. |
| 6,540,746 B1 | 4/2003 | Bhler et al. |
| 6,547,793 B1 | 4/2003 | McGuire |
| 6,676,662 B1 | 1/2004 | Bagga et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,786,909 B1 | 9/2004 | Dransfeld et al. |
| 6,796,986 B2 | 9/2004 | Duffner |
| 6,859,661 B2 | 2/2005 | Tuke |
| 7,018,383 B2 | 3/2006 | McGuire |
| 7,033,361 B2 | 4/2006 | Collazo |
| 7,037,309 B2 | 5/2006 | Weil et al. |
| 7,097,647 B2 | 8/2006 | Segler et al. |
| 7,112,204 B2 | 9/2006 | Justin et al. |
| 7,153,310 B2 | 12/2006 | Ralph et al. |
| 7,175,667 B2 | 2/2007 | Saunders et al. |
| 7,182,766 B1 | 2/2007 | Mogul |
| 7,229,445 B2 | 6/2007 | Hayeck et al. |
| 7,241,298 B2 | 7/2007 | Nemec et al. |
| 7,282,054 B2 | 10/2007 | Steffensmeier et al. |
| 7,344,538 B2 | 3/2008 | Myerson et al. |
| 7,377,924 B2 | 5/2008 | Raistrick et al. |
| 7,465,303 B2 | 12/2008 | Riccione et al. |
| 7,537,596 B2 | 5/2009 | Jensen |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,695,473 B2 | 4/2010 | Ralph et al. |
| 7,763,026 B2 | 7/2010 | Egger et al. |
| 7,785,355 B2 | 8/2010 | Mohr et al. |
| D629,900 S | 12/2010 | Fisher |
| 7,931,680 B2 | 4/2011 | Myerson et al. |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,083,746 B2 | 12/2011 | Novak |
| 8,123,753 B2 | 2/2012 | Poncet |
| 8,133,283 B2 | 3/2012 | Wilson |
| 8,137,406 B2 | 3/2012 | Novak et al. |
| 8,147,530 B2 | 4/2012 | Strnad et al. |
| 8,162,996 B2 | 4/2012 | Schelling |
| 8,167,918 B2 | 5/2012 | Strnad et al. |
| 8,172,848 B2 | 5/2012 | Tomko et al. |
| 8,172,884 B2 | 5/2012 | Bouman |
| 8,172,886 B2 | 5/2012 | Castaneda et al. |
| 8,177,819 B2 | 5/2012 | Medoff |
| 8,177,820 B2 | 5/2012 | Anapliotis et al. |
| 8,177,822 B2 | 5/2012 | Medoff |
| 8,192,441 B2 | 6/2012 | Collazo |
| 8,197,487 B2 | 6/2012 | Poncet et al. |
| 8,231,623 B1 | 7/2012 | Jordan |
| 8,231,662 B2 | 7/2012 | Huebner |
| 8,231,663 B2 | 7/2012 | Kay et al. |
| 8,235,994 B2 | 8/2012 | Hollawell |
| 8,236,000 B2 | 8/2012 | Ammann et al. |

(56) References Cited

U.S. PATENT DOCUMENTS

| | | |
|---|---|---|
| 8,236,034 B2 | 8/2012 | Binder et al. |
| 8,241,338 B2 | 8/2012 | Castaneda et al. |
| 8,246,561 B1 | 8/2012 | Agee et al. |
| 8,246,661 B2 | 8/2012 | Beutter et al. |
| D666,721 S | 9/2012 | Wright et al. |
| 8,257,403 B2 | 9/2012 | Den Hartog et al. |
| 8,257,405 B2 | 9/2012 | Haidukewych et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plassky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Buescher |
| 8,382,807 B2 | 2/2013 | Austin et al. |
| 8,398,687 B2 | 3/2013 | Vasta et al. |
| 8,403,966 B2 | 3/2013 | Ralph et al. |
| D679,395 S | 4/2013 | Wright et al. |
| 8,409,209 B2 | 4/2013 | Ammann et al. |
| 8,435,246 B2 | 5/2013 | Fisher et al. |
| 8,444,679 B2 | 5/2013 | Ralph et al. |
| 8,475,462 B2 | 7/2013 | Thomas et al. |
| 8,496,662 B2 | 7/2013 | Novak et al. |
| 8,496,690 B2 | 7/2013 | Sixto et al. |
| 8,512,339 B2 | 8/2013 | Medoff et al. |
| 8,518,045 B2 | 8/2013 | Szanto |
| 8,523,870 B2 | 9/2013 | Green, II et al. |
| 8,529,571 B2 | 9/2013 | Horan et al. |
| 8,529,608 B2 | 9/2013 | Terrill et al. |
| 8,540,777 B2 | 9/2013 | Ammann et al. |
| 8,545,508 B2 | 10/2013 | Collazo |
| 8,545,540 B2 | 10/2013 | Castaneda et al. |
| D694,884 S | 12/2013 | Mooradian et al. |
| D695,402 S | 12/2013 | Dacosta et al. |
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,702,715 B2 | 4/2014 | Ammann et al. |
| 8,702,762 B2 | 4/2014 | Jacene et al. |
| D705,929 S | 5/2014 | Frey |
| 8,715,363 B2 | 5/2014 | Ratron et al. |
| 8,728,084 B2 | 5/2014 | Berelsman et al. |
| 8,734,492 B2 | 5/2014 | Mohr et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,764,807 B2 | 7/2014 | Michel et al. |
| 8,771,279 B2 | 7/2014 | Philippon et al. |
| 8,777,948 B2 | 7/2014 | Bernsteiner |
| 8,784,427 B2 | 7/2014 | Fallin et al. |
| 8,784,457 B2 | 7/2014 | Graham |
| 8,784,498 B2 | 7/2014 | Scheland |
| 8,795,286 B2 | 8/2014 | Sand et al. |
| 8,801,727 B2 | 8/2014 | Chan et al. |
| 8,808,303 B2 | 8/2014 | Stemniski et al. |
| 8,808,334 B2 | 8/2014 | Strnad et al. |
| 8,828,012 B2 | 9/2014 | May et al. |
| 8,828,063 B2 | 9/2014 | Blitz et al. |
| 8,834,532 B2 | 9/2014 | Velikov et al. |
| 8,834,537 B2 | 9/2014 | Castaneda et al. |
| 8,852,249 B2 | 10/2014 | Ahrens et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| 8,888,824 B2 | 11/2014 | Austin et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,940,026 B2 | 1/2015 | Hilse et al. |
| 8,940,029 B2 | 1/2015 | Leung et al. |
| 8,945,132 B2 | 2/2015 | Plassy et al. |
| 8,998,903 B2 | 4/2015 | Price et al. |
| 8,998,904 B2 | 4/2015 | Zeetser et al. |
| 9,023,052 B2 | 5/2015 | Lietz et al. |
| 9,044,250 B2 | 6/2015 | Olsen et al. |
| 9,060,822 B2 | 6/2015 | Lewis et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| 9,138,244 B2 | 9/2015 | Mebarak et al. |
| D740,424 S | 10/2015 | Dacosta et al. |
| 9,149,313 B2 | 10/2015 | Strnad et al. |
| 9,220,515 B2 | 12/2015 | Castaneda et al. |
| 9,271,769 B2 | 3/2016 | Batsch et al. |
| 9,375,242 B2 | 6/2016 | Worcel |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |
| 9,452,057 B2 | 9/2016 | Dacosta et al. |
| 9,522,023 B2 | 11/2016 | Taddad et al. |
| 9,592,084 B2 | 3/2017 | Grant |
| 9,622,805 B2 | 4/2017 | Santrock et al. |
| 9,642,656 B2 | 5/2017 | Kotuljac et al. |
| 9,668,793 B2 | 6/2017 | Gaudin |
| 9,750,538 B2 | 9/2017 | Soffiatti et al. |
| 9,785,747 B2 | 10/2017 | Geebelen |
| 9,867,642 B2 | 1/2018 | Simon |
| 9,936,994 B2 | 4/2018 | Smith et al. |
| 9,980,760 B2 | 5/2018 | Dacosta et al. |
| 10,028,750 B2 | 7/2018 | Rose |
| 10,064,631 B2 | 9/2018 | Dacosta et al. |
| 10,159,499 B2 | 12/2018 | Dacosta et al. |
| 10,226,287 B2 | 3/2019 | Langford et al. |
| 10,238,437 B2 | 3/2019 | Simon |
| 10,245,088 B2 | 4/2019 | Dayton et al. |
| 10,292,713 B2 | 5/2019 | Fallin et al. |
| 10,327,829 B2 | 6/2019 | Dacosta et al. |
| 10,376,268 B2 | 8/2019 | Fallin et al. |
| 10,470,779 B2 | 11/2019 | Fallin et al. |
| 10,849,631 B2 * | 12/2020 | Hatch ............... A61B 17/1739 |
| 11,304,705 B2 | 4/2022 | Fallin et al. |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2003/0060827 A1 | 3/2003 | CoughIn |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0116930 A1 | 6/2004 | O'Driscoll et al. |
| 2004/0138669 A1 | 7/2004 | Horn |
| 2005/0004676 A1 | 1/2005 | Schon et al. |
| 2005/0033430 A1 | 2/2005 | Powers et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0192578 A1 | 9/2005 | Horst |
| 2005/0228389 A1 | 10/2005 | Stiernborg |
| 2005/0251147 A1 | 11/2005 | Novak |
| 2005/0267482 A1 | 12/2005 | Hyde |
| 2005/0273112 A1 | 12/2005 | McNamara |
| 2006/0116679 A1 | 6/2006 | Lutz et al. |
| 2006/0129163 A1 | 6/2006 | McGuire |
| 2006/0149264 A1 | 7/2006 | Castaneda et al. |
| 2006/0206044 A1 | 9/2006 | Simon |
| 2006/0217733 A1 | 9/2006 | Plassky et al. |
| 2006/0229621 A1 | 10/2006 | Cadmus |
| 2006/0235397 A1 | 10/2006 | Sanders et al. |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2006/0276795 A1 | 12/2006 | Orbay et al. |

(56) References Cited

U.S. PATENT DOCUMENTS

| | | |
|---|---|---|
| 2007/0010818 A1 | 1/2007 | Stone et al. |
| 2007/0055249 A1 | 3/2007 | Jensen et al. |
| 2007/0123857 A1 | 5/2007 | Deffenbaugh et al. |
| 2007/0123884 A1 | 5/2007 | Abdou |
| 2007/0191848 A1 | 8/2007 | Wack et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0015591 A1 | 1/2008 | Castaneda et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0118768 A1 | 5/2009 | Sixto, Jr. et al. |
| 2009/0198244 A1 | 8/2009 | Leibel |
| 2009/0198279 A1 | 8/2009 | Zhang et al. |
| 2009/0210010 A1 | 8/2009 | Strnad et al. |
| 2009/0210013 A1 | 8/2009 | Kay et al. |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0281543 A1 | 11/2009 | Orbay et al. |
| 2009/0287309 A1 | 11/2009 | Walch et al. |
| 2010/0004691 A1 | 1/2010 | Amato et al. |
| 2010/0023010 A1 | 1/2010 | Nelson et al. |
| 2010/0069910 A1 | 3/2010 | Hasselman |
| 2010/0121334 A1 | 5/2010 | Couture et al. |
| 2010/0125300 A1 | 5/2010 | Blitz et al. |
| 2010/0130981 A1 | 5/2010 | Richards |
| 2010/0152752 A1* | 6/2010 | Denove ............... A61B 17/842 606/228 |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0008745 A1 | 1/2011 | McQuillan et al. |
| 2011/0009865 A1 | 1/2011 | Orfaly |
| 2011/0087295 A1 | 4/2011 | Kubiak et al. |
| 2011/0093017 A1 | 4/2011 | Prasad et al. |
| 2011/0093084 A1 | 4/2011 | Morton |
| 2011/0118739 A1 | 5/2011 | Tyber et al. |
| 2011/0137351 A1 | 6/2011 | Huebner et al. |
| 2011/0166607 A1 | 7/2011 | Castaneda et al. |
| 2011/0178524 A1 | 7/2011 | Lawrence et al. |
| 2011/0245835 A1 | 10/2011 | Dodds et al. |
| 2011/0264149 A1 | 10/2011 | Pappalardo et al. |
| 2011/0288550 A1 | 11/2011 | Orbay et al. |
| 2011/0301648 A1 | 12/2011 | Lofthouse et al. |
| 2011/0301653 A1* | 12/2011 | Reed ............... A61B 17/8883 606/319 |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265204 A1 | 10/2012 | Schmierer et al. |
| 2012/0265301 A1 | 10/2012 | Demers et al. |
| 2012/0277745 A1 | 11/2012 | Lizee |
| 2012/0303033 A1 | 11/2012 | Weiner et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0090695 A1 | 4/2013 | Bernstein et al. |
| 2013/0096563 A1 | 4/2013 | Meade et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Tatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0238032 A1 | 9/2013 | Schilter |
| 2013/0238093 A1* | 9/2013 | Mauldin ............ A61B 17/1671 623/16.11 |
| 2013/0261670 A1 | 10/2013 | Laeng et al. |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0012887 A1 | 1/2014 | Tamano |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0052193 A1 | 2/2014 | Prandi et al. |
| 2014/0074099 A1 | 3/2014 | Vigneron et al. |
| 2014/0074101 A1 | 3/2014 | Collazo |
| 2014/0081341 A1 | 3/2014 | Lin et al. |
| 2014/0094861 A1 | 4/2014 | Fallin |
| 2014/0094924 A1 | 4/2014 | Tacking et al. |
| 2014/0107650 A1 | 4/2014 | Dacosta et al. |
| 2014/0107798 A1 | 4/2014 | Jeng et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0172021 A1 | 6/2014 | Castaneda et al. |
| 2014/0180342 A1 | 6/2014 | Lowery et al. |
| 2014/0180343 A1 | 6/2014 | Gaudin |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0214093 A1 | 7/2014 | Courtney et al. |
| 2014/0249537 A1 | 9/2014 | Wong et al. |
| 2014/0257291 A1 | 9/2014 | Houff |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |

(56) References Cited

U.S. PATENT DOCUMENTS

| | | |
|---|---|---|
| 2014/0350561 A1 | 11/2014 | Dacosta et al. |
| 2015/0032168 A1 | 1/2015 | Orsak et al. |
| 2015/0039033 A1 | 2/2015 | Biedermann |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2015/0313652 A1 | 11/2015 | Burckhardt et al. |
| 2015/0335366 A1 | 11/2015 | Dacosta et al. |
| 2015/0359580 A1 | 12/2015 | Dacosta et al. |
| 2016/0015426 A1 | 1/2016 | Dayton |
| 2016/0022315 A1 | 1/2016 | Soffiatti et al. |
| 2016/0030098 A1 | 2/2016 | Dacosta et al. |
| 2016/0030106 A1* | 2/2016 | Carter ............... A61B 17/3417 606/38 |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0192970 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1* | 8/2016 | Hatch ................. A61B 17/151 |
| 2016/0235454 A1 | 8/2016 | Treace et al. |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0354127 A1 | 12/2016 | Lundquist et al. |
| 2017/0014143 A1 | 1/2017 | Dayton et al. |
| 2017/0014173 A1* | 1/2017 | Smith ................ A61B 17/1739 |
| 2017/0042598 A1 | 2/2017 | Santrock et al. |
| 2017/0042599 A1* | 2/2017 | Bays ................. A61B 17/1739 |
| 2017/0079669 A1 | 3/2017 | Bays et al. |
| 2017/0143511 A1 | 5/2017 | Cachia |
| 2017/0164989 A1 | 6/2017 | Weiner et al. |
| 2018/0132868 A1 | 5/2018 | Dacosta et al. |
| 2018/0140339 A1 | 5/2018 | Silva et al. |
| 2018/0344334 A1 | 12/2018 | Kim et al. |
| 2018/0344371 A1 | 12/2018 | Monk et al. |
| 2019/0357950 A1 | 11/2019 | Bernstein et al. |
| 2020/0015856 A1* | 1/2020 | Treace ............... A61B 17/7291 |
| 2020/0015870 A1 | 1/2020 | Treace |
| 2020/0281637 A1* | 9/2020 | Denham ............... A61B 17/68 |
| 2021/0022879 A1* | 1/2021 | Hollis ................ A61B 17/151 |
| 2021/0282828 A1* | 9/2021 | Champagne ....... A61B 17/7291 |

FOREIGN PATENT DOCUMENTS

| | | |
|---|---|---|
| CA | 2491824 A1 | 9/2005 |
| CA | 2854997 A1 | 5/2013 |
| CA | 2715491 C | 4/2014 |
| CH | 695846 A5 | 9/2006 |
| CN | 2701408 Y | 5/2005 |
| CN | 2930668 Y | 8/2007 |
| CN | 201558162 U | 8/2010 |
| CN | 101836888 A | 9/2010 |
| CN | 201572172 U | 9/2010 |
| CN | 201586060 U | 9/2010 |
| CN | 201912210 U | 8/2011 |
| CN | 102755186 A | 10/2012 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 103892954 A | 7/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2389884 B1 | 7/2013 |
| EP | 2441406 B1 | 9/2013 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| EP | 3023068 A2 | 5/2016 |
| ES | 2379929 S | 5/2012 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 2154143 A | 9/1985 |
| GB | 2154144 A | 9/1985 |
| GB | 2334214 B | 1/2003 |
| IL | 184773 A | 8/2012 |
| IN | 200607174 P1 | 8/2007 |
| IN | 200903719 P1 | 6/2009 |
| IN | 200904479 P2 | 5/2010 |
| IN | 140/DELNP/2012 | 2/2013 |
| IN | 2004/KOLNP/2013 | 11/2013 |
| JP | S635739 A | 1/1988 |
| JP | H07313522 A | 12/1995 |
| JP | 2004174265 A | 6/2004 |
| JP | 2006158972 A | 6/2006 |
| JP | 4134243 B2 | 8/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| KR | 101081268 B1 | 11/2011 |
| MD | 756 Z | 11/2014 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004024009 A1 | 3/2004 |
| WO | 2004089227 A2 | 10/2004 |
| WO | 2006065512 A1 | 6/2006 |
| WO | 2007006430 A1 | 1/2007 |
| WO | 2007106962 A1 | 9/2007 |
| WO | 2008029142 A2 | 3/2008 |
| WO | 2008029143 A2 | 3/2008 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |

(56) References Cited

FOREIGN PATENT DOCUMENTS

| | | | |
|---|---|---|---|
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015094410 A1 | 6/2015 |
| WO | 2015105880 A1 | 7/2015 |
| WO | 2015127515 A2 | 9/2015 |
| WO | 2016003477 A1 | 1/2016 |
| WO | 2016134160 A1 | 8/2016 |
| WO | 2017205512 A1 | 11/2017 |
| ZA | 200808914 B | 2/2012 |

OTHER PUBLICATIONS

NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"RAYHACK Ulnar Shortening Generation II Low-Profile Locking System Surgical Technique," Wright Medical Technology, Inc., Dec. 2013, 20 pages.
Rx-Fix Mini Rail External Fixator, Wright Medical Technology, Brochure, Aug. 15, 2014, 2 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.
Siddiqui et al. "Fixation of Metatarsal Fracture With Bone Plate in a Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.

Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
"Smith & Nephew scores a HAT-TRICK with its entry into the high-growth hammer toe repair market," Smith & Nephew, Jul. 31, 2014, 2 pages.
Stableloc External Fixation System, Acumed, Product Overview, Effective date Sep. 2015, 4 pages.
Stahl et al., "Derotation of Post-Traumatic Femoral Deformities by Closed Intramedullary Sawing," Injury, vol. 37, No. 2, Feb. 2006, pp. 145-151, (Abstract Only).
Talbot et al., "Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Tricot et al., "3D-corrective osteotomy using surgical guides for posttraumatic distal humeral deformity," Acta Orthopaedica Belgica, vol. 78, No. 4, 2012, pp. 538-542.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 663-566, including English Abstract on p. 564.
Vitek, "Neue Techniken in der Fußchirurgie Das V-tek-System," ABW Wissenschaftsverlag GmbH, 2009, 11 pages, Including English Abstract.
Weber et al., "A Simple System for Navigation of Bone Alignment Osteotomies of the Tibia," International Congress Series, vol. 1268, Jan. 2004, pp. 608-613, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP—Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Acumed, "Acu-Loc Wrist Plating System," Brochure and Surgical Technique, effective date Apr. 2012, reported publication date Sep. 23, 2013, 19 pages.
Acumed, "Hand Fracture System," Brochure, effective date Sep. 2014, reported publication date Jan. 29, 2016, 6 pages.
Acumed, "Hub Cap Fusion Plates," Retrieved from <http://www.acumed.net/products/hand-wrist/carpal/hub-cap-fusion-plates>, 2016, 8 pages.
Arthrex, "Double Compression Plates," Retrieved from <https://www.arthrex.com/foot-ankle/double-compression-plates>, 2016, 3 pages.
Arthrex, "Plantar Lapidus Plate," 2015, 6 pages.
Arthrex, "Proximal Metatarsal Osteotomy using Plates," Retrieved from <http://www.arthrex.com/foot-ankle/proximal-metatarsal-osteotomy-using-plates>, 2016, 2 pages.
Chang et al., "Lapidus Arthrodesis: A Different Perspective," Journal of the American Podiatric Medical Association, vol. 84, No. 6, Jun. 1994, pp. 281-288.

(56) References Cited

OTHER PUBLICATIONS

Couzens et al., "Stainless Steel Versus Titanium Volar Multi-Axial Locking Plates for Fixation of Distal Radius Fractures: A Randomised Clinical Trial," BMC Musculoskeletal Disorders, vol. 15, No. 74, Mar. 2014, 7 pages.
Diaconu et al., "Locking Plates for Fixation of Extra-Articular Fractures of the First Metacarpal Base: A Series of 15 Cases," Chirurgie de la Main, vol. 30, No. 1, pp. 26-30, Abstract only.
Horton et al., "Deformity Correction and Arthrodesis of the Midfoot with a Medial Plate," Foot & Ankle, vol. 14, No. 9, Nov./Dec. 1993, pp. 493-499.
Merete GMBH, "MetaFix OpenWedge," Retrieved from <http://www.merete-medical.com/de/produkte/fuss/hallux-valgus/metafixr-openwedge.html>, 2016, 4 pages (Google Translation).
Osteomed, "ExtremiLock Ankle Plating System," Brochure, published prior to Nov. 20, 2014, 6 pages.
Osteomed, "ExtremiLock Foot Plating System," Brochure, published prior to Nov. 20, 2014, 6 pages.
Osteomed, "Hand Plating System," Brochure, published prior to Nov. 20, 2014, 8 pages.
Plaass et al, "Anterior Double Plating for Rigid Fixation of Isolated Tibiotalar Arthrodesis," Foot and Ankle International, vol. 30, No. 7, Jul. 2009, pp. 631-639.
Plaass et al., "Placement of Plantar Plates for Lapidus Arthrodesis: Anatomical Considerations," Foot and Ankle International, vol. 37, No. 4, Apr. 2016, pp. 427-432.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Wienke et al., "Bone Stimulation for Nonunions: What the Evidence Reveals," Podiatry Today, vol. 24, No. 9, Sep. 2011, pp. 52-57.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "A User-Friendly Method of Pin Site Management for External Fixators," Foot and Ankle Specialist, Sep. 16, 2011, 4 pages.
Dayton et al., "Effectiveness of a Locking Plate in Preserving Midcalcaneal Length and Positional Outcome after vans Calcaneal Osteotomy: A Retrospective Pilot Study," The Journal of Foot and Ankle Surgery, vol. 52, 2013, pp. 710-713.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "Clarification of the Anatomic Definition of the Bunion Deformity," The Journal of Foot and Ankle Surgery, vol. 53, 2014, pp. 160-163.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Catanese et al., "Measuring Sesamoid Position in Hallux Valgus: When Is the Sesamoid Axial View Necessary," oot and Ankle Specialist, 2014, 3 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the iterature," The Journal of Foot and Ankle Surgery, Article in Press, 2015, 3 pages.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Diseas of the First Metatarsalphalangeal Joint," Podiatry Management, Jan. 2013, pp. 137-142.
DeCarbo et al., "Locking Plates: Do They Prevent Complications?," Podiatry Today, Apr. 2014, 7 pages.
Easley et al., "Current Concepts Review: Hallux Valgus Part II: Operative Treatment," Foot and Ankle International, vol. 28, No. 6, Jun. 2007, pp. 748-758.
Kim et lal., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Easley et al., "What is the Best Treatment for Hallux Valgus?," Evidence-Based Orthopaedics—The Best Answers to Clinical Questions, Chapter 73, 2009, pp. 479-491.
Shurnas et al., "Proximal Metatarsal Opening Wedge Osteotomy," Operative Techniques in Foot and Ankle Surgery, Section I, Chapter 13, 2011, pp. 73-78.
Coetzee et al., "Revision Hallux Valgus Correction," Operative Techniques in Foot and Ankle Surgery, Section I, Chapter 15, 2011, pp. 84-96.

(56) References Cited

OTHER PUBLICATIONS

Le et al., "Tarsometatarsal Arthrodesis," Operative Techniques in Foot and Ankle Surgery, Section II, Chapter 40, 2011, pp. 281-285.
Collan et al., "The biomechanics of the first metatarsal bone in hallux valgus: A preliminary study utilizing a weight bearing extremity CT," Foot and Ankle Surgery, vol. 19, 2013, pp. 155-161.
Eustace et al., "Hallux valgus, first metatarsal pronation and collapse of the medial longitudinal arch—a radiological correlation," Skeletal Radiology, vol. 23, 1994, pp. 191-194.
Mizuno et al., "Detorsion Osteotomy of the First Metatarsal Bone in Hallux Valgus," Japanese Orthopaedic Association, Tokyo, 1956; 30:813-819.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
D'Amico et al., "Motion of the First Ray: Clarification Through Investigation," Journal of the American Podiatry Association, vol. 69, No. 1, Jan. 1979, pp. 17-23.
Groves, "Operative Report," St. Tammany Parish Hospital, Date of Procedure, Mar. 26, 2014, 2 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Defendant Fusion Orthopedics LLC's Invalidity Contentions, No. CV-22-00490-PHX-SRB, US District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.
Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile ocking Plate,"Orthopaedics and Traumatology, vol. 7, 1999, pp. 133-143.
Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
Didomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.
Fallin et al., US Provisional Application Entitled Indexed Tri-Planar Osteotomy Guide and Method, U.S. Appl. No. 62/118,378, filed Feb. 19, 2015, 62 pages.
Fishco, "A Straightforward Guide To The Lapidus Bunionectomy,"Podiatry Today, Retrieved online from <https://www.hmpgloballearningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Gerard et al., "The Modified Lapidus Procedure," Orthopedics, vol. 31, No. 3, Mar. 2008, 7 pages.
Giannoudis et al., "Hallux Valgus Correction," Practical Procedures in Elective Orthopaedic Surgery, Pelvis and Lower Extremity, Chapter 38, 2012, 22 pages.
Greiner, "The Jargon of Pedal Movements," Foot & Ankle International, vol. 28, No. 1, Jan. 2007, pp. 109-125.
Groves, "Functional Position Joint Sectioning: Pre-Load Method for Lapidus Arthrodesis," The Podiatry Institute, Update 2015, Chapter 6, 2015, pp. 23-29.
Hardy et al., "Observations on Hallux Valgus," The Journal of Bone and Joint Surgery, vol. 33B, No. 3, Aug. 1951, pp. 376-391.

(56) References Cited

OTHER PUBLICATIONS

Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.

Integra, "Integra Large Qwix Positioning and Fixation Screw, Surgical Technique," 2012, 16 pages.

Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.

Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.

Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.

Myerson, "Cuneiform-Metatarsal Arthrodesis," The Foot and Ankle, Chapter 9, 1997, pp. 107-117.

Sammarco, "Surgical Strategies: Mau Osteotomy for Correction of Moderate and Severe Hallux Valgus Deformity," Foot & Ankle International, vol. 28, No. 7, Jul. 2007, pp. 857-864.

Schon et al., "Cuneiform-Metatarsal Arthrodesis for Hallux Valgus, "The Foot and Ankle, Second Edition, Chapter 8, 2002, pp. 99-117.

Sokoloff, "Lapidus Procedure," Textbook of Bunion Surgery, Chapter 15, 1981, pp. 277-287.

Stamatis et al., "Mini Locking Plate as "Medial Buttress" for Oblique Osteotomy for Hallux Valgus," Foot & Ankle International, vol. 31, No. 10, Oct. 2010, pp. 920-922.

Stewart, "Use for BME Speed Nitinol Staple Fixation for the Lapidus Procedure," date unknown, 1 page.

Wukich et al., "Hypermobility of the First Tarsometatarsal Joint," Foot and Ankle Clinics, vol. 10, No. 1, Mar. 2005, pp. 157-166.

Dayton et al., "Biwinged Excision for Round Pedal Lesions," The Journal of Foot and Ankle Surgery, vol. 35, No. 3, 1996, pp. 244-249.

Dayton et al., "Medial Incision Approach to the First Metatarsophalangeal Joint," The Journal of Foot and Ankle Surgery, vol. 40, No. 6, Nov./Dec. 2001, pp. 414-417.

Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.

Dayton et al., "Use of the Z Osteotomy for Tailor Bunionectomy," The Journal of Foot and Ankle Surgery, vol. 42, No. 3, May/Jun. 2003, pp. 167-169.

Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.

"Accu-Cut Osteotomy Guide System," BioPro, Brochure, Oct. 2018, 2 pages.

"Acumed Osteotomiesystem Operationstechnik," Acumed, 2014, 19 pages (including 3 pages English translation).

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.

Alvine et al., "Peg and Dowel Fusion of the Proximal Interphalangeal Joint," Foot & Ankle, vol. 1, No. 2, 1980, pp. 90-94.

Anderson et al., "Uncemented STAR Total Ankle Prostheses," The Journal of Bone and Joint Surgery, vol. 86(1, Suppl 2), Sep. 2004, pp. 103-111, (Abstract Only).

Bednarz et al., "Modified Lapidus Procedure for the Treatment of Hypermobile Hallux Valgus," Foot & Ankle International, vol. 21, No. 10, Oct. 2000, pp. 816-821.

Blomer, "Knieendoprothetik—Herstellerische Probleme und technologische Entwicklungen," Orthopade, vol. 29, 2000, pp. 688-696, including English Abstract on p. 689.

Bouaicha et al., "Fixation of Maximal Shift Scarf Osteotomy with Inside Out Plating: Technique Tip," Foot & Ankle International, vol. 32, No. 5, May 2011, pp. 567-569.

Carr et al., "Correctional Osteotomy for Metatarsus Primus Varus and Hallux Valgus," The Journal of Bone and Joint Surgery, vol. 50-A, No. 7, Oct. 1968, pp. 1353-1367.

Coetzee et al., "The Lapidus Procedure: A Prospective Cohort Outcome Study," Foot & Ankle International, vol. 25, No. 8, Aug. 2004, pp. 526-531.

Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot and Ankle Surgery, vol. 52, No. 3, May/Jun. 2013, pp. 348-354.

Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).

Doty et al., "Hallux valgus and hypermobility of the first ray: facts and fiction," International Orthopaedics, vol. 37, 2013, pp. 1655-1660.

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.

Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.

"Futura Forefoot Implant Arthroplasty Products," Tornier, Inc., 2008, 14 pages.

Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.

Garthwait, "Accu-Cut System Facilitates Enhanced Precision," Podiatry Today, vol. 18, No. 6, Jun. 2005, 6 pages.

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Gotte, "Entwicklung eines Assistenzrobotersystems für die Knieendoprothetik," Forschungsberichte, Technische Universitat Munchen, 165, 2002, 11 pages, including partial English Translation.

Gregg et al., "Plantar plate repair and Weil osteotomy for metatarsophalangeal joint instability," Foot and Ankle Surgery, vol. 13, 2007, pp. 116-121.

(56) References Cited

OTHER PUBLICATIONS

Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"HAT-TRICK Lesser Toe Repair System," Smith & Nephew, Brochure, Aug. 2014, 12 pages.
"HAT-TRICK Lesser Toe Repair System, Foot and Ankle Technique Guide, Metatarsal Shortening Osteotomy Surgical Technique," Smith & Nephew, 2014, 16 pages.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Mortier et al., "Axial Rotation of the First Metatarsal Head in a Normal Population and Hallux Valgus Patients," Orthopaedics and Traumatology: Surgery and Research, vol. 98, 2012, pp. 677-683.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
"Lag Screw Target Bow," Stryker Leibinger GmbH & Co. KG, Germany 2004, 8 pages.
Lapidus, "The Author's Bunion Operation From 1931 to 1959," Clinical Orthopaedics, vol. 16, 1960, pp. 119-135.
Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, "Computernavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Hallux-valgus-Deformität mittels IVP-Plattenfixateur (V-TEK-System)," Operative Orthopädie und Traumatologie, vol. 26, No. 2, 2014, pp. 184-195, including English Abstract on p. 186.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect of Ankle Flexion Angle on Axial Alignment of Total Ankle Replacement," Foot and Ankle International, vol. 31, No. 12, Dec. 2010, pp. 1093-1098, (Abstract Only).
Rochet et al., "Proximal Ulna Comminuted Fractures: Fixation Using a Double-Plating Technique," Revue de Chirurgie Orthopédique et Traumatologique, vol. 96, No. 7, Nov. 2010, pp. 800-807.
Smith & Nephew, Inc, "D-RAD Smart Pack," Single-Use Volar Distal Radius Plating System, Brochure, Jun. 2014, 8 pages.
Smith & Nephew, Inc, "Evos Mini," Plating System, Brochure, May 2015, 12 pages.
Smith & Nephew, Inc, "Proximal Humerus Locking Plate," Peri-Loc Upper Extremity Locked Plating System, Surgical Technique, Sep. 2006, 36 pages.
Smith & Nephew, Inc, "Medial Column Fusion for Midfoot Deformity Correction," VLP Foot Variable Angle Locked Plating System, Surgical Technique, 2013, 20 pages.
Stryker, "Anchorage Plating System," Operative Technique, Rev. 2, Aug. 2015, 32 pages.
Stryker, "VariAx Foot Locked Plating System," Jun. 2008, 25 pages.
Synthes, "LCP Periprosthetic System," 2009, 8 pages.
Tornier, "Hand and Wrist," Retrieved from <http://www.tornier-us.com/upper/hand/>, 2016, 1 page.
Tornier, "CoverLoc Volar Plate," Retrieved from < http://www.tornier-us.com/upper/hand/writra003/>, 2016, 2 pages.
Tornier, "DFX Distal Fibula and DTX Distal Tibia Plates," Retrieved from < http://www.tornier-us.com/lower/ankle/anktra003/>, 2016, 2 pages.
Tornier, "CalcLock Extreme," Retrieved from < http://www.tornier-us.com/lower/foot/footra011/>, 2014, 2 pages.
Vilex, "The Vilex Plate System," Brochure, 2011, 4 pages.
Wright Medical Group N.V., "Foot & Ankle," Retrieved from < http://www.wright.com/physicians/foot-ankle>, 2016, 4 pages.
Wright Medical Group N.V., "Darco Modular Rearfoot System (MRS) LPS Lapidus Plating System," Brochure, Aug. 2016, 1 page.
Zimmer, Inc. "Foot and Ankle Solutions," Retrieved from <http://www.zimmer.com/medical-professionals/products/foot-and-ankle.html>, 2014, 3 pages.

\* cited by examiner

MULTI-DIAMETER K-WIRE FOR ORTHOPEDIC APPLICATIONS

RELATED MATTERS

This application claims the benefit of U.S. Provisional Application No. 62/900,391, filed Sep. 13, 2019, the entire contents of which are incorporated herein by reference.

TECHNICAL FIELD

This disclosure relates to orthopedic devices and techniques.

BACKGROUND

Kirschner wires, or K-wires, are sterilized, sharpened, smooth or threaded metal pins configured for a variety of medical, orthopedic, dental, and plastic surgical procedures, as well as various types of veterinary surgeries. K-wires can be used to hold bone fragments together and/or to provide an anchor for skeletal traction. A K-wire may be driven into bone using a powered or hand drill.

Example applications in which K-wires may be used include procedures for realigning comparatively small bones within in the human body, such as bones in the hand or foot. These bones may be misaligned and require anatomical realignment with the aid of a K-wire during a surgical procedure. For example, one common type of bone deformity is hallux valgus, which is a progressive foot deformity in which the first metatarsophalangeal joint is affected and is often accompanied by significant functional disability and foot pain. The metatarsophalangeal joint is laterally deviated, resulting in an abduction of the first metatarsal while the phalanges adduct. This often leads to development of soft tissue and a bony prominence on the medial side of the foot, which is called a bunion. Surgical intervention may be used to correct a bunion deformity.

SUMMARY

In general, this disclosure is directed to multi-diameter fixation pins for orthopedic procedures, such as multi-diameters K-wires, and techniques utilizing such a fixation pin. A multi-diameter fixation pin can be inserted into a bone during an orthopedic procedure, such as inserted through one bone portion into an adjacent bone portion to fixate the two bone portions relative to each other. The two bone portions may be different portions of the same bone (e.g., separated by a cut or fracture) or different two different bones. In either case, a multi-diameter fixation pin according to the disclosure may include a leading diameter sized for the specific orthopedic procedure being undertaken and/or the size of the bone into which the fixation pin is being inserted. The multi-diameter fixation pin may also include a trailing diameter different than the leading diameter. The trailing diameter may be sized for use with a specific sized powered driver. For example, in orthopedic procedures that involve inserting larger diameter pins and smaller diameter pins into bone(s), all pins used in the procedure may have a trailing diameter (e.g., the larger diameter or the smaller diameter) that allows the pins to be inserted with the same powered driver (e.g., the same attachment head) without needing different sized drivers or attachment heads for different sized pins.

As an example implementation, a clinician may select a powered driver and/or a collet for the powered driver that is configured to receive a certain size fixation pin or certain range of sizes of fixation pins. For example, the clinician may from select one collet for the powered driver from a set of different collets, each of which is sized to receive a different size fixation pin (or range of sizes). The clinician can insert the selected collet into the powered driver. The clinician can then use the powered driver with selected collet to insert multiple fixation pins into one or more bone portions during a procedure.

The clinician can insert a fixation pin having a size acceptable for use with the selected collet into the powered driver and then use the powered driver to drive the fixation pin into one or more bone portions. The fixation pin can have a constant (e.g., same) diameter over it length, e.g., optionally with narrowing or other shaping features adjacent the tip. Before or after inserting the fixation pin with constant diameter into the powered driver and then into a bone portion, the clinician may also wish to insert a fixation pin into a bone portion having a diameter outside of the size acceptable for use with the selected collet. Traditionally, this would require the clinician to obtain a different powered driver or change the collet on the powered driver, necessitating additional time and procedural steps.

A multi-diameter fixation pin according to some examples of the present disclosure can be configured with a driver engagement portion and a bone insertion portion. The driver engagement portion can have a diameter different (smaller or larger) than the bone insertion portion. The driver engagement portion may have a size corresponding to the size of one or more other constant diameter fixation pins used during the surgical procedure. The driver engagement portion of the multi-diameter fixation pin can have a size acceptable for use with the selected collet of the powered driver that is appropriately sized for receiving and driving one or more other constant diameter fixation pins. However, the bone insertion portion of the multi-diameter fixation pin can have a different diameter. As a result, the clinician can insert the multi-diameter fixation pin into the powered driver without changing drivers and/or collets used for inserting one or more other fixation pins during the procedure and insert a portion of the multi-diameter fixation pin into one or more bone portions that has a size not otherwise acceptable for use with the collet and/or driver.

In one example, a method is described that includes inserting a pin having a first diameter into a collet of a powered driver and driving the pin into at least one of a metatarsal and a cuneiform. The method further involves moving the metatarsal relative to the cuneiform to establish a moved position of the metatarsal. The method also includes inserting a driver engagement portion of a multi-diameter fixation pin into the collet of the driver and driving a bone insertion portion of the multi-diameter fixation pin through the metatarsal and into another bone to hold the moved position of the metatarsal. The example specifies that the collet of the powered driver is sized to receive the pin having the first diameter and the driver engagement portion of the multi-diameter fixation pin but not the bone insertion portion of the multi-diameter fixation pin.

In another example, a method is described that includes inserting a driver engagement portion of a multi-diameter fixation pin into a collet of a powered driver and driving a bone insertion portion of the multi-diameter fixation pin through one or more bone portions. The example specifies that the collet of the powered driver is sized to receive the driver engagement portion of the multi-diameter fixation pin but not the bone insertion portion of the multi-diameter fixation pin.

In another example, a surgical fixation wire is described. The surgical fixation wire has a body extending from a first end to a second end opposite the first end. The body defines a driver engagement portion having a first diameter and a bone insertion portion having a second diameter less than the first diameter. The example specifies that the first end of the body defines a tip configured for insertion into a bone and the driver engagement portion is configured for insertion into a powered driver.

The details of one or more examples are set forth in the accompanying drawings and the description below. Other features, objects, and advantages will be apparent from the description and drawings, and from the claims.

DETAILED DESCRIPTION

Figure 1B:
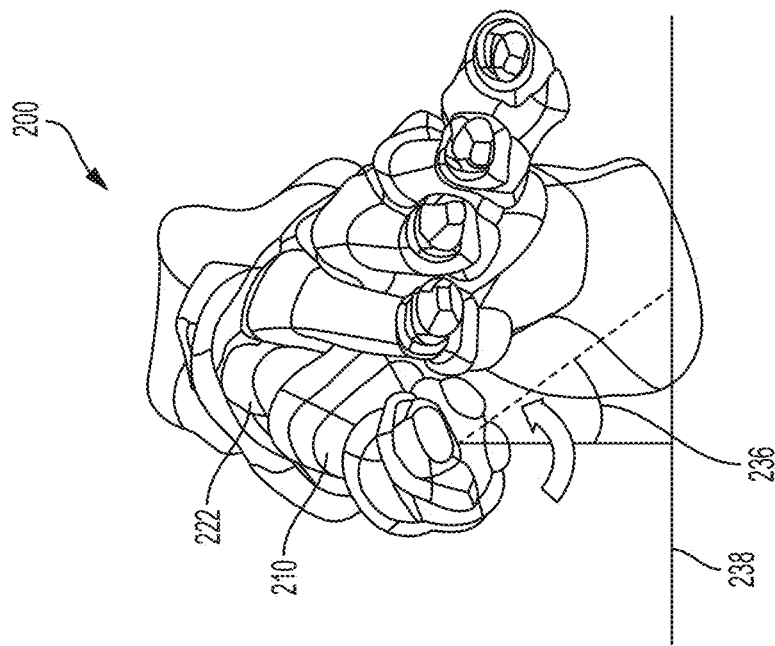
FIGS. 1A and 1B are front views of a foot showing a normal first metatarsal position and an example frontal plane rotational misalignment position, respectively.

In general, this disclosure is directed to fixation pins used during orthopedic procedures and techniques utilizing such fixation pins. As used herein, the terms "fixation pin" and "fixation wire" are generally used interchangeably. In practice, clinicians may generally refer to fixation pins having a comparatively small diameter (e.g., 1.6 mm or less) as a fixation wire and fixation pins having a comparatively larger diameter is just a fixation pin. However, the specific nomenclature choice between pin and wire can vary between clinicians and providers. Accordingly, multi-diameter fixation pins as described herein can also embrace multi-diameter fixation wires. Example embodiments of the fixation pins include multi-diameter Kirschner wires, or K-wires, and multi-diameter Steinmann pins.

A multi-diameter fixation pin as described herein can be used in any desired orthopedic procedure, including procedures utilizing only a single fixation pin or procedures utilizing multiple fixation pins (which may all be multi-diameter fixation pins as described herein or a combination of multi-diameter fixation pins and constant diameter fixation pins). The multi-diameter fixation pin can be inserted into a single bone portion or into multiple bone portions when used during the orthopedic procedure. For example, the multi-diameter fixation pin may be inserted through one bone portion and into an adjacent bone portion. The two bone portions may be different portions of the same bone (e.g., separated by a cut or fracture). Alternatively, the two bone portions may be different bones, such as to adjacent bones separated by a joint space.

In an example implementation, a multi-diameter fixation pin can be used during a surgical joint realignment procedure. For example, a multi-diameter fixation pin can be used during a surgical procedure, such as a bone alignment, osteotomy, fusion procedure, and/or other procedures where one or more bones are to be prepared (e.g., cartilage or bone removal and/or cut). Such a procedure can be performed, for example, on bones (e.g., adjacent bones separated by a joint or different portions of a single bone) in the foot or hand, where bones are relatively smaller compared to bones in other parts of the human anatomy. In one example, a procedure utilizing a multi-diameter fixation pin can be performed to correct an alignment between a metatarsal (e.g., a first metatarsal) and a second metatarsal and/or a cuneiform (e.g., a medial, or first, cuneiform), such as in a bunion correction surgery. An example of such a procedure is a Lapidus procedure (also known as a first tarsal-metatarsal fusion). In another example, the procedure can be performed by modifying an alignment of a metatarsal (e.g., a first metatarsal). An example of such a procedure is a basilar metatarsal osteotomy procedure.

A multi-diameter fixation pin may be used with one or more other instruments, such as a bone positioning guide and/or a bone preparation guide. The bone preparation guide may be pinned by one or more fixation pins to one or more bone portions to facilitate preparation of adjacent bone portions for fusion. The bone positioning guide may be used to impart a force to one bone portion to move the bone portion relative to another bone portion.

In some examples, one or more multi-diameter fixation pins are used during a realignment procedure in which a metatarsal (e.g., first metatarsal) is moved relative to and oppose cuneiform across a tarsal-metatarsal joint to establish a moved position of the metatarsal. One or more constant diameter fixation pins (fixation pins not having a multiple diameter) may be used during the surgical procedure. The constant diameter fixation pin(s) may have a diameter different (e.g., smaller or larger) than the diameter of the bone insertion portion of the multi-diameter fixation pin. Accordingly, use of the multi-diameter fixation pin can allow the clinician to insert a fixation pin having a different diameter than the constant diameter fixation pins into one or more bone portions during the surgical procedure without changing driver hardware.

Figure 1A:
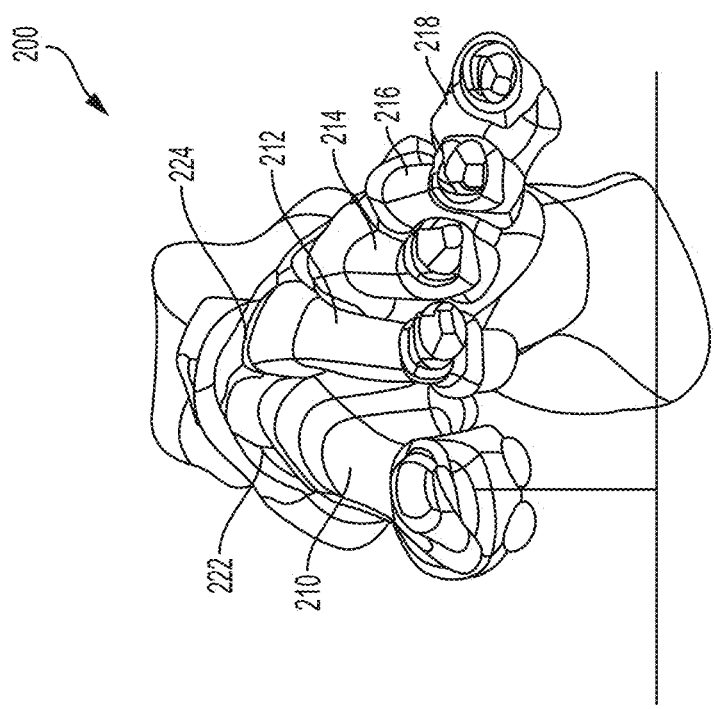
Figure 2B:
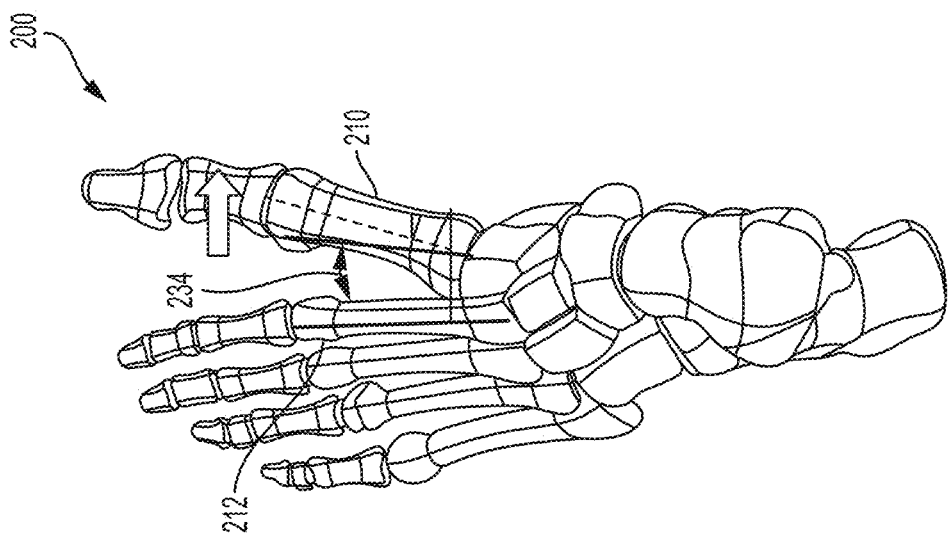
FIGS. 2A and 2B are top views of a foot showing a normal first metatarsal position and an example transverse plane misalignment position, respectively.
Figure 2A:
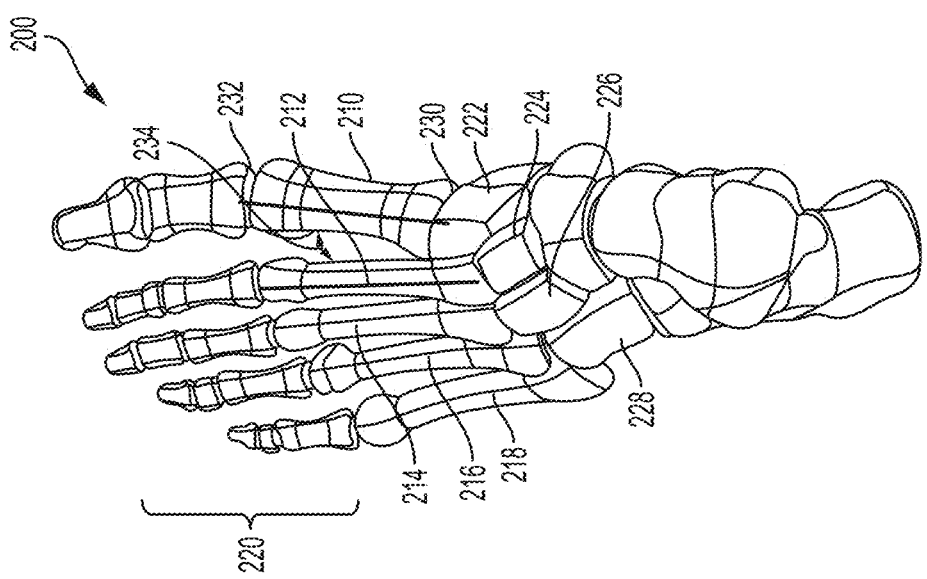
Figure 3B:
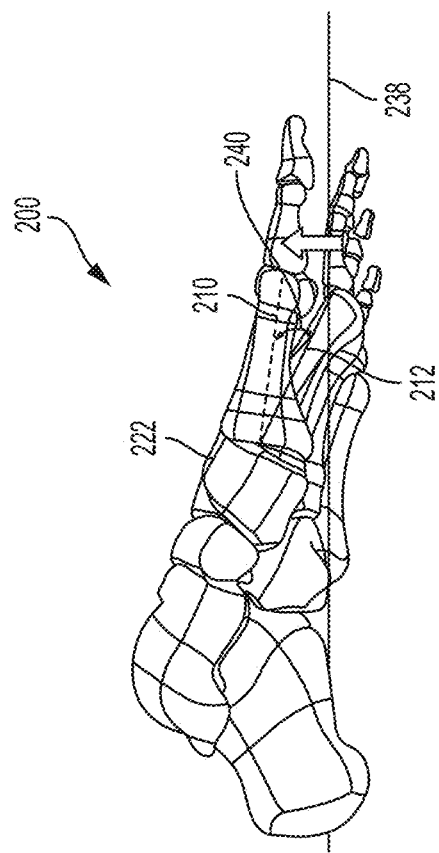
FIGS. 3A and 3B are side views of a foot showing a normal first metatarsal position and an example sagittal plane misalignment position, respectively.
Figure 3A:
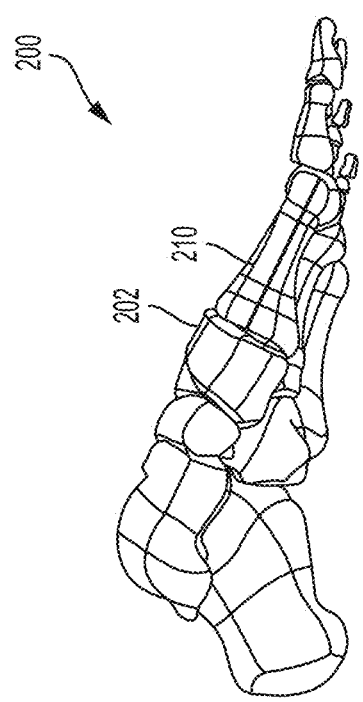

FIGS. 1-3 are different views of a foot 200 showing example anatomical misalignments that may occur and be corrected according to the present disclosure. Such misalignment may be caused by a hallux valgus (bunion), natural growth deformity, or other condition causing anatomical misalignment. FIGS. 1A and 1B are front views of foot 200 showing a normal first metatarsal position and an example frontal plane rotational misalignment position, respectively. FIGS. 2A and 2B are top views of foot 200 showing a normal first metatarsal position and an example transverse plane misalignment position, respectively. FIGS. 3A and 3B are side views of foot 200 showing a normal first metatarsal position and an example sagittal plane misalignment position, respectively. While FIGS. 1B, 2B, and 3B show each respective planar misalignment in isolation, in practice, a metatarsal may be misaligned in any two of the three planes or even all three planes. Accordingly, it should be appreciated that the depiction of a single plane misalignment in each of FIGS. 1B, 2B, and 3B is for purposes of illustration and a metatarsal may be misaligned in multiple planes that is desirably corrected.

With reference to FIGS. 1A and 2A, foot 200 is composed of multiple bones including a first metatarsal 210, a second metatarsal 212, a third metatarsal 214, a fourth metatarsal 216, and a fifth metatarsal 218. The metatarsals are connected distally to phalanges 220 and, more particularly, each to a respective proximal phalanx. The first metatarsal 210 is connected proximally to a medial cuneiform 222, while the second metatarsal 212 is connected proximally to an intermediate cuneiform 224 and the third metatarsal is connected proximally to lateral cuneiform 226. The fourth and fifth metatarsals 216, 218 are connected proximally to the cuboid bone 228. The joint 230 between a metatarsal and respective cuneiform (e.g., first metatarsal 210 and medial cuneiform 222) is referred to as the tarsometatarsal ("TMT") joint. The joint 232 between a metatarsal and respective proximal phalanx is referred to as a metatarsophalangeal joint. The angle 234 between adjacent metatarsals (e.g., first metatarsal 210 and second metatarsal 212) is referred to as the intermetatarsal angle ("IMA").

As noted, FIG. 1A is a frontal plane view of foot 200 showing a typical position for first metatarsal 210. The frontal plane, which is also known as the coronal plane, is generally considered any vertical plane that divides the body into anterior and posterior sections. On foot 200, the frontal plane is a plane that extends vertically and is perpendicular to an axis extending proximally to distally along the length of the foot. FIG. 1A shows first metatarsal 210 in a typical rotational position in the frontal plane. FIG. 1B shows first metatarsal 210 with a frontal plane rotational deformity characterized by a rotational angle 236 relative to ground, as indicated by line 238.

FIG. 2A is a top view of foot 200 showing a typical position of first metatarsal 210 in the transverse plane. The transverse plane, which is also known as the horizontal plane, axial plane, or transaxial plane, is considered any plane that divides the body into superior and inferior parts. On foot 200, the transverse plane is a plane that extends horizontally and is perpendicular to an axis extending dorsally to plantarly (top to bottom) across the foot. FIG. 2A shows first metatarsal 210 with a typical IMA 234 in the transverse plane. FIG. 2B shows first metatarsal 210 with a transverse plane rotational deformity characterized by a greater IMA caused by the distal end of first metatarsal 210 being pivoted medially relative to the second metatarsal 212.

FIG. 3A is a side view of foot 200 showing a typical position of first metatarsal 210 in the sagittal plane. The sagittal plane is a plane parallel to the sagittal suture which divides the body into right and left halves. On foot 200, the sagittal plane is a plane that extends vertically and is perpendicular to an axis extending proximally to distally along the length of the foot. FIG. 3A shows first metatarsal 210 with a typical rotational position in the sagittal plane. FIG. 3B shows first metatarsal 210 with a sagittal plane rotational deformity characterized by a rotational angle 240 relative to ground, as indicated by line 238.

A system and technique that utilizes a compressor-distractor and/or a pin lock according to the disclosure can be useful during a bone positioning procedure, for example, to correct an anatomical misalignment of a bones or bones. In some applications, the compressor-distractor can help establish and/or maintain a realignment between a metatarsal and an adjacent cuneiform. Additionally or alternatively, the compressor-distractor can facilitate clean-up and compression between adjacent bone portions between fixation. The pin lock can help hold the compressor-distractor at an appropriate position along the length of a pin or pins connecting the compressor-distractor to bone portions to be compressed and/or distracted.

The metatarsal undergoing realignment may be anatomically misaligned in the frontal plane, transverse plane, and/or sagittal plane, as illustrated and discussed with respect to FIGS. 1-3 above. Accordingly, realignment may involve releasing the misaligned metatarsal for realignment and thereafter realigning the metatarsal in one or more planes, two or more planes, or all three planes. After suitably realigning the metatarsal, the metatarsal can be fixated to hold and maintain the realigned positioned.

While a metatarsal can have a variety of anatomically aligned and misaligned positions, in some examples, the term "anatomically aligned position" means that an angle of a long axis of first metatarsal 210 relative to the long axis of second metatarsal 212 is about 10 degrees or less (e.g., 9 degrees or less) in the transverse plane and/or sagittal plane. In certain embodiments, anatomical misalignment can be corrected in both the transverse plane and the frontal plane. In the transverse plane, a normal IMA 234 between first metatarsal 210 and second metatarsal 212 is less than about 9 degrees. An IMA 234 of between about 9 degrees and about 13 degrees is considered a mild misalignment of the first metatarsal and the second metatarsal. An IMA 234 of greater than about 16 degrees is considered a severe misalignment of the first metatarsal and the second metatarsal. In some embodiments, methods and/or devices according to the disclosure are utilized to anatomically align first metatarsal 210 by reducing the IMA from over 10 degrees to about 10 degrees or less (e.g., to an IMA of 9 degrees or less, or an IMA of about 1-5 degrees), including to negative angles of about −5 degrees or until interference with the second metatarsal, by positioning the first metatarsal at a different angle with respect to the second metatarsal.

With respect to the frontal plane, a normal first metatarsal will be positioned such that its *crista* prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal may be axially rotated between about 4 degrees to about 30 degrees or more. In some embodiments, methods and/or devices according to the disclosure are utilized to anatomically align the metatarsal by reducing the metatarsal rotation from about 4 degrees or more to less than 4 degrees (e.g., to about 0 to 2 degrees) by rotating the metatarsal with respect to the adjacent cuneiform.

A multi-diameter fixation pin and technique that utilizes a multi-diameter fixation pin according to the disclosure can be useful during a bone positioning procedure, for example, to correct an anatomical misalignment of a bones or bones. In some applications, the multi-diameter fixation pin can be used to help hold a moved position of a metatarsal relative to an adjacent cuneiform. For example, after a metatarsal is moved relative to an adjacent cuneiform, the multi-diameter fixation pin may be inserted into the move metatarsal and adjacent bone (e.g., through a first metatarsal and into an adjacent second metatarsal). This can provide temporary fixation helping to hold the move position of the metatarsal (e.g., first metatarsal) for further procedural steps, such as applying one or more permanent fixation devices (e.g., plate, screw, intramedullary pin).

The metatarsal undergoing realignment may be anatomically misaligned in the frontal plane, transverse plane, and/or sagittal plane, as illustrated and discussed with respect to FIGS. 1-3 above. Accordingly, realignment may involve releasing the misaligned metatarsal for realignment and thereafter realigning the metatarsal in one or more planes, two or more planes, or all three planes. After suitably realigning the metatarsal, the metatarsal can be fixated to hold and maintain the realigned positioned.

While a metatarsal can have a variety of anatomically aligned and misaligned positions, in some examples, the term "anatomically aligned position" means that an angle of a long axis of first metatarsal 210 relative to the long axis of second metatarsal 212 is about 10 degrees or less (e.g., 9 degrees or less) in the transverse plane and/or sagittal plane. In certain embodiments, anatomical misalignment can be corrected in both the transverse plane and the frontal plane. In the transverse plane, a normal IMA 234 between first metatarsal 210 and second metatarsal 212 is less than about 9 degrees. An IMA 234 of between about 9 degrees and about 13 degrees is considered a mild misalignment of the first metatarsal and the second metatarsal. An IMA 234 of greater than about 16 degrees is considered a severe misalignment of the first metatarsal and the second metatarsal. In some embodiments, methods and/or devices according to the disclosure are utilized to anatomically align first metatarsal 210 by reducing the IMA from over 10 degrees to about 10 degrees or less (e.g., to an IMA of 9 degrees or less, or an IMA of about 1-5 degrees), including to negative angles of about −5 degrees or until interference with the second metatarsal, by positioning the first metatarsal at a different angle with respect to the second metatarsal.

With respect to the frontal plane, a normal first metatarsal will be positioned such that its *crista* prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal may be axially rotated between about 4 degrees to about 30 degrees or more. In some embodiments, methods and/or devices according to the disclosure are utilized to anatomically align the metatarsal by reducing the metatarsal rotation from about 4 degrees or more to less than 4 degrees (e.g., to about 0 to 2 degrees) by rotating the metatarsal with respect to the adjacent cuneiform.

An example technique utilizing a multi-diameter fixation pin will be described in greater detail below with respect to FIGS. 9-15. However, example multi-diameter fixation pin that may be used according to the disclosure will first be described with respect to FIGS. 4 and 5.

Figure 4:
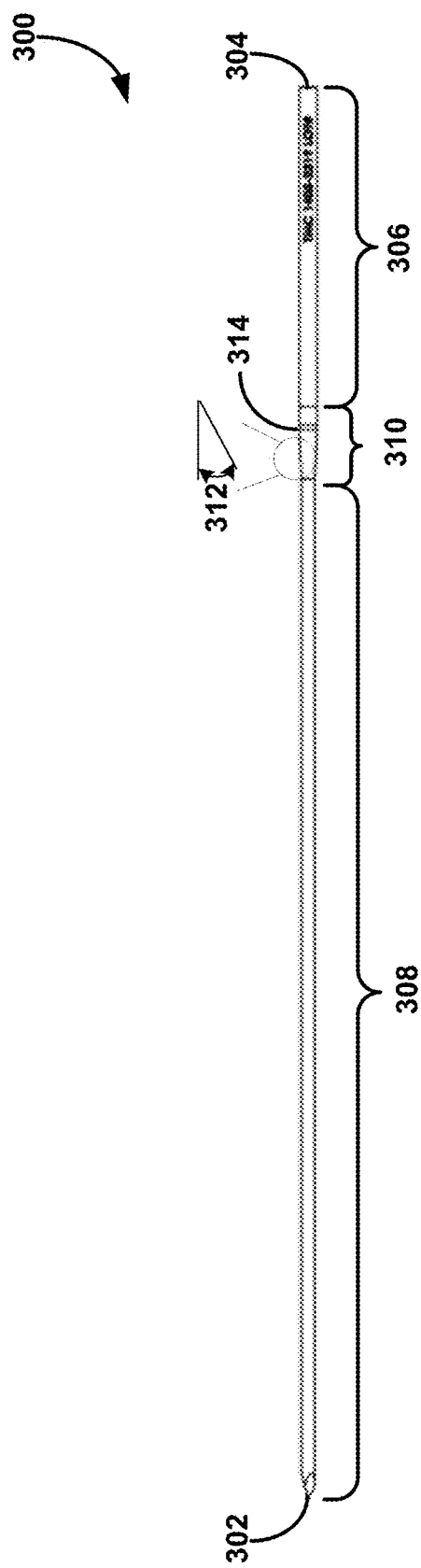
FIG. 4 is an illustration of an example multi-diameter fixation pin according to disclosure.

FIG. 4 is an illustration of an example multi-diameter fixation pin 300 for an orthopedic procedure. Fixation pin 300 has a body extending lengthwise from a first end 302 to a second and 304 at an opposite end of the body. Fixation pin 300 defines a driver engagement portion 306 and a bone insertion portion 308. Driver engagement portion 306 and bone insertion portion 308 may be different portions of the fixation pin having different cross-sectional areas (e.g., diameters).

For example, driver engagement portion 306 of fixation pin 300 can be configured (e.g., sized and/or shaped) for insertion into a powered driver. The driver engagement portion 306 may have a length and diameter that allows the driver engagement portion to be inserted into a powered driver to a depth appropriate for the powered driver to then act on the fixation pin for driving the pin a surgical procedure Bone insertion portion 308 a fixation pin 300 can be configured to be partially or fully inserted into one or more bone portions. For example, bone insertion portion 308 may have a diameter different than driver engagement portion 306. In some implementations, bone insertion portion 308 has a diameter smaller than the diameter of driver engagement portion 306. When so configured, a comparatively larger region a fixation pin 300 defined by driver engagement portion 306 can be inserted into the powered driver. A comparatively smaller region a fixation pin 300 defined by bone insertion portion 308 can be partially or fully inserted into and/or through one or more bone portions.

Depending on the procedure being undertaken, it may be clinically beneficial to insert a comparatively smaller diameter fixation pin into the one or more bone portions than a comparatively larger diameter fixation pin. The smaller diameter fixation pin may cause less bone trauma. Additionally or alternatively, in instances where the fixation pin is inserted into comparatively small bones, such as bones of the foot (e.g., cuneiform, first metatarsal, second metatarsal), a comparatively smaller fixation pin may reduce the tendency of the bone(s) to fracture or break upon insertion of a fixation pin. Such fracturing or breaking may occur when a comparatively large fixation pin is inserted into the bone(s).

While fixation pin 300 is described as having a driver engagement portion 306, it should be appreciated that the entire portion need not be inserted into a driver during a surgical procedure. Rather, driver engagement portion 306 may define a section along the length of fixation pin 300 having a first diameter different than one or more other sections of the fixation pin having one or more other diameters. Driver engagement portion 306 may or may not include second end 304.

Likewise, it should be appreciated that while fixation pin 300 is described as having a bone insertion portion 308, the entire portion need not be inserted into a bone during a surgical procedure. Rather, bone insertion portion 308 may define a section along the length of fixation pin 300 having a second diameter different than driver engagement portion 306. At least part of the length of bone insertion portion 308 may be inserted into and/or through one or more bone portions during a surgical procedure.

Fixation pin 300 in some examples, driver engagement portion 306 and bone insertion portion 308 a fixation pin 300 are immediately adjacent to each other along the length of the fixation pin. A sharp (e.g., 90 degree) transition may be provided between driver engagement portion 306 and bone insertion portion 308, such as a dimensional instep or out step between the two differently sized portions. In other configurations, fixation pin 300 to define a taper portion between driver engagement portion 306 and bone insertion portion 308. The taper portion may be a region of dimensional transition between the cross-sectional size of driver engagement portion 306 and the cross-sectional size of bone insertion portion 308.

In the example of FIG. 4, fixation pin 300 is illustrated as including a taper portion 310 sandwiched between driver engagement portion 306 and bone insertion portion 308. Taper portion 310 can have a size (e.g., diameter) that transitions from the cross-sectional size of driver engagement portion 306 to the cross-sectional size of bone insertion portion 308. Taper portion 310 may taper at any suitable angle 312. In some implementations, angle 312 ranges from 5° to 75°, such as from 10° to 60°, or from 15° to 45°.

In some examples, fixation pin 300 may include an indicator 314 positioned at a location along the length of the fixation pin. Indicator 314 may designate how deep fixation pin 300 can be inserted into a powered driver. For example, in use, a clinician may insert second end 304 of fixation pin 300 into a powered driver and advance the fixation pin deeper into the body (e.g., collet) up to indicator. The clinician may not advance fixation pin 300 beyond indicator 314 into the driver. When configured with indicator 314, the indicator may be implemented in a variety of different ways. As one example, a color band or marking may be provided on a perimeter surface of fixation pin 300. As another example, a notch may be formed in a perimeter surface of fixation pin 300. For instance, a laser scribe may be formed partially or fully about a circumferential perimeter of fixation pin 300 to define indicator 314.

As noted, multi-diameter fixation pin 300 includes first end 302. First end 302 is the leading end of the fixation pin that is inserted into bone during a procedure. In some examples, first end 302 is tapered/sharpened to a point or rounded. This may help ease insertion of the pin during a surgical procedure. In other examples, first end 302 of fixation pin 300 is not shaped relative to a remainder of bone insertion portion 308.

The specific dimensions of fixation pin 300 can vary depending on the needs of the clinician in the desired procedure in which the fixation pin is going to be utilized. In some examples, driver engagement portion 306 of fixation pin 300 is sized to have a same diameter as one or more other pins used in a surgical procedure (wherein the pins have a constant diameter across their length instead of having multiple diameters). Additionally or alternatively, driver engagement portion 306 of fixation pin 300 may be sized to have a diameter that is different than but sufficiently close to the diameter of one or more other pins used in the surgical procedure such that the fixation pin can be inserted into bone using the same powered driver hardware used to insert the one or more other pins.

Bone insertion portion 308 can have a different diameter (e.g., smaller diameter) than driver engagement portion 306. The diameter of bone insertion portion 308 may be sufficiently different than the diameter of driver engagement portion 306 such that, if the entire length of fixation pin 300 had the diameter of bone insertion portion 308, the fixation pin could not be inserted into bone using the same powered driver hardware used to insert the one or more other pins used in a surgical procedure (wherein the pins have a constant diameter across their length instead of having multiple diameters).

As examples, driver engagement portion 306 may define a first diameter greater than or equal to 2.0 mm, such as a diameter within a range from 2.0 mm to 3.2 mm. Bone insertion portion 308 may define a second diameter less than 2.0 mm, such as a diameter within a range from 0.7 mm to 1.8 mm. Independent of the specific diameters of driver engagement portion 306 and bone insertion portion 308, the difference between the diameters of the two portions may be at least 0.1 mm, such as at least 0.2 mm, or at least 0.5 mm. For example, the difference between the diameters of driver engagement portion 306 and bone insertion portion 308 may range from 0.1 mm to 1.5 mm, such as from 0.2 mm to 0.5 mm.

One or more other pins used in a surgical procedure with fixation pin 300 (wherein the one or more other pins have a constant diameter across their length instead of having multiple diameters) can have a diameter the same as and/or within the same range of as those listed above with respect to driver engagement portion 306. In some examples, the one or more other pins used in the surgical procedure have a diameter that differs from the diameter of driver engagement portion 306 by less than 0.5 mm, such as less than 0.2 mm.

The overall length of multi-diameter fixation pin 300 from first end 302 to second end 304 can also vary depending on the desired clinical application. In different examples, fixation pin 300 may have a length within a range from 25 mm to 500 mm, such as from 50 mm to 260 mm. Further, while fixation pin 300 may typically have a circular cross-sectional shape, the fixation pin can have any polygonal (e.g., square, rectangle) or arcuate (e.g., curved, elliptical) shape.

Fixation pin 300 may be formed as a unitary body from a single piece of material, e.g., via casting, molding, and/or milling. Alternatively, fixation pin 300 may be formed from multiple segments of material (e.g., materials having different diameters) that are then joined together to form a unitary body (e.g., via welding or other permanent joining) technique. In general, fixation pin 300 can be formed from a biocompatible material. Example materials that may be used to fabricate fixation pin 300 include steel (e.g., stainless steel), titanium, ceramic materials, biocompatible plastics, and combinations thereof. After fabrication, fixation pin 300 may be packaged and sterilized, e.g., chemically and/or thermally. Fixation pin 300 may be packaged alone or as part of a kit that includes one or more other pins and/or other instruments used during a surgical procedure.

Multi-diameter fixation pin 300 can be inserted into one or more bone portions using a powered driver. The powered driver may receive the fixation pin by inserting driver engagement portion 306 into the driver and then applying a force to the pin to drive bone insertion portion 308 of the pin into and/or through one or more bone portions. The powered driver may apply a rotary force, causing rotation of the fixation pin, and/or an axial impact force to drive the pin actually into the bone.

Figure 5:
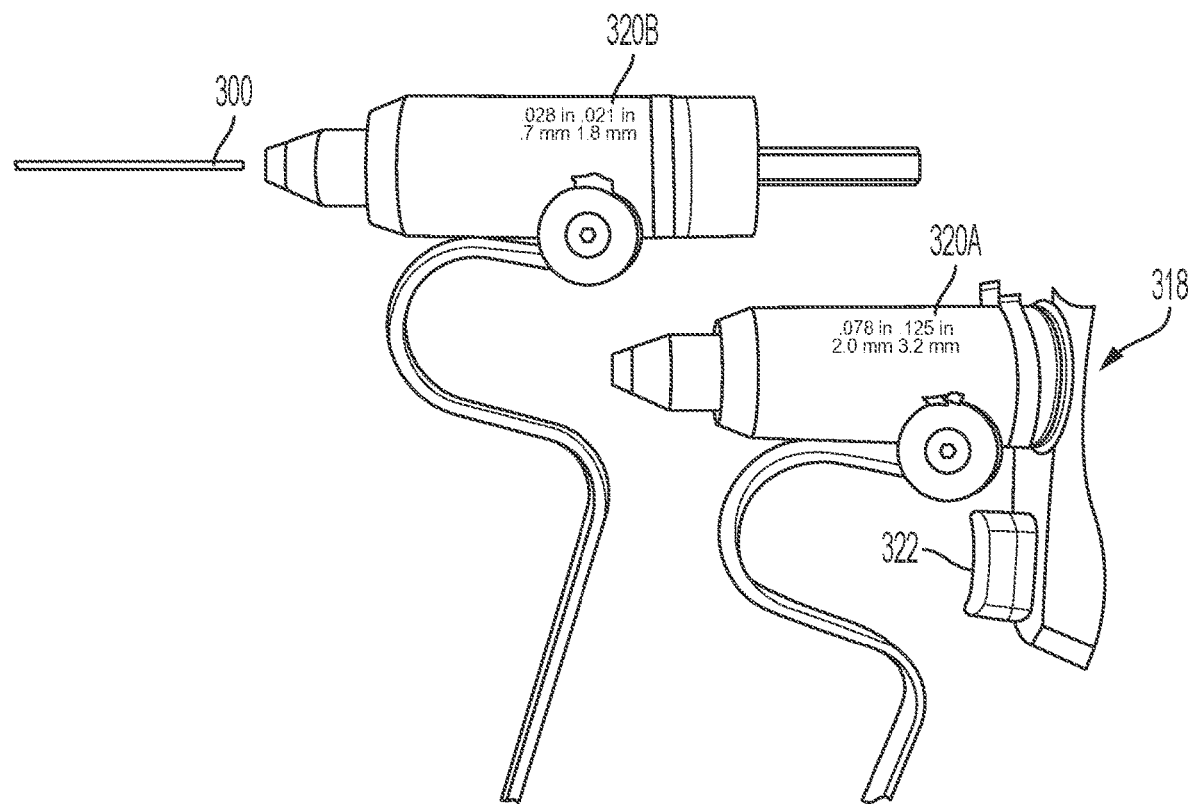
FIG. 5 is an illustration of an example powered driver system that can be used to drive the multi-diameter fixation pin of FIG. 4.

FIG. 5 is an illustration of an example system that includes a powered driver 318 that can be used to insert fixation pin 300. Powered driver 318 in this example is shown with interchangeable collets 320A and 320B (collectively referred to as "collet 320"). Collet 320 may be a chuck that forms a collar around an object (e.g., fixation pin 300 and one or more other fixation pins optionally used during a surgical procedure) and can exert a clamping force on the object. Collet 320 can have a sleeve with a cylindrical inner surface. The collet may be squeezed against a matching taper such that its inner surface contracts to a slightly smaller diameter, squeezing a pin inserted therein to hold the pin securely.

Powered driver 318 can have an integral collet 320 that can only receive a specific size or range of sizes of fixation pins. Alternatively, powered driver 318 can have interchangeable collets 320, each of which is configured to receive a different specific size or range of sizes of fixation pins.

Powered driver 318 can be powered by any motive energy, such as a pneumatic energy or electrical energy. To engage powered driver 318, the clinician may depress trigger 322 to drive a fixation pin 300 inserted into the powered driver into a bone. While fixation pin 300 is generally described as being inserted into a bone using a powered driver, such as powered driver 318, it should be appreciated that a fixation pin according to disclosure is not limited to such an example insertion device. For example, the multi-diameter fixation pin can be inserted using hand force or a powered driver having a different configuration than that illustrated and described with respect to FIG. 5.

In some examples, a multi-diameter fixation pin is used as part of a metatarsal realignment procedure in which a metatarsal is realigned relative to an adjacent cuneiform and/or metatarsal in one or more planes, such as two or three planes. Additional details on example bone realignment techniques and devices with which the multi-diameter fixation pin may be used are described in U.S. Pat. No. 9,622,805, titled "BONE POSITIONING AND PREPARING GUIDE SYSTEMS AND METHODS," filed on Dec. 28, 2015 and issued Apr. 18, 2017, and U.S. Pat. No. 9,936,994, titled "BONE POSITIONING GUIDE," filed on Jul. 14, 2016 and issued on Apr. 10, 2018, and US Patent Publication No. 2017/0042599 titled "TARSAL-METATARSAL JOINT PROCEDURE UTILIZING FULCRUM," filed on Aug. 14, 2016. The entire contents of each of these documents are hereby incorporated by reference.

A multi-diameter fixation pin can be used in any desired orthopedic procedure, and the disclosure is not limited to any particular procedure. In some implementations, however, the multi-diameter fixation pin is used as part of a metatarsal realignment procedure. The metatarsal realignment procedure may or may not utilize one or more other surgical instruments, such as a bone positioning guide and/or a bone preparation guide.

Figure 6:
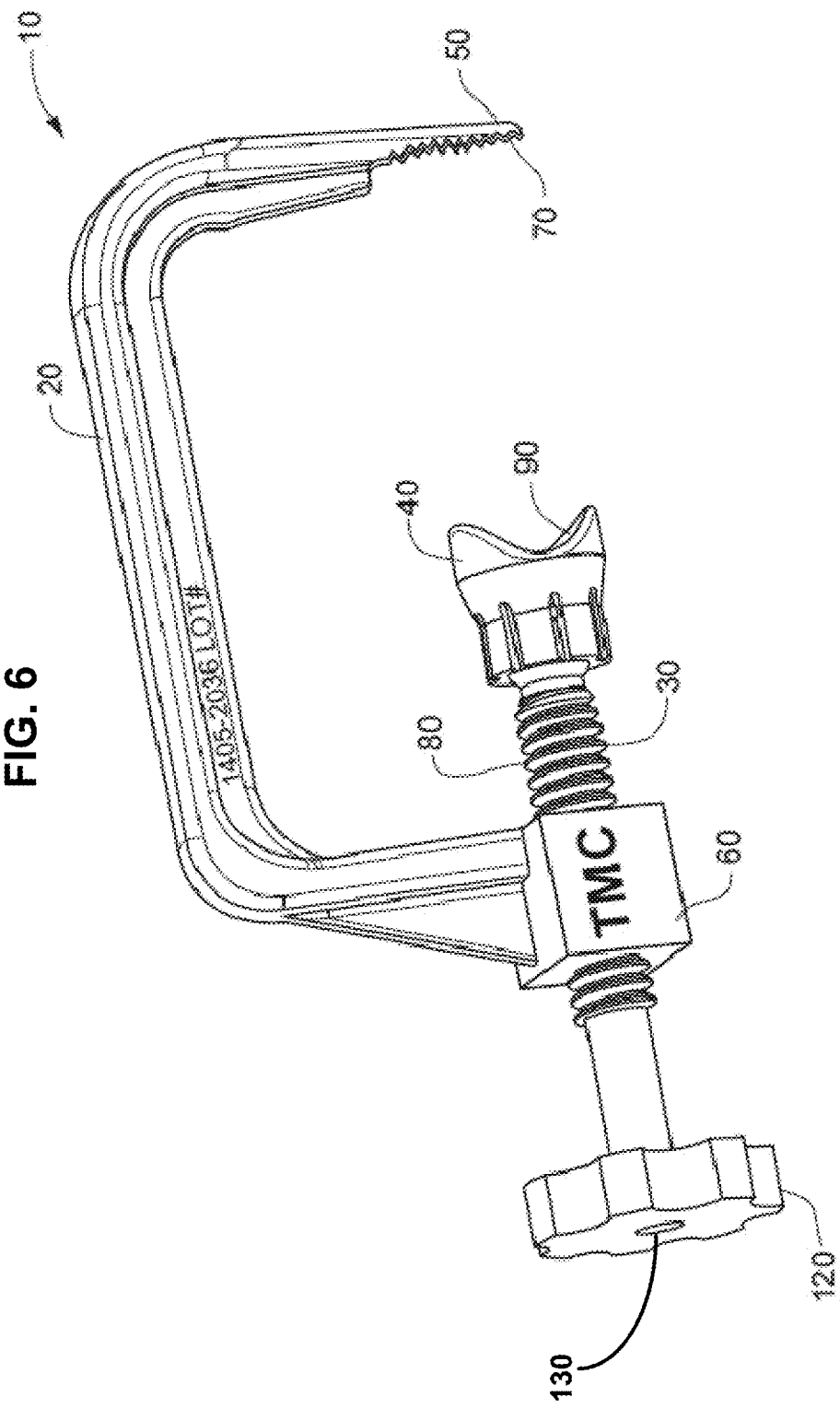
FIG. 6 is a side perspective view of an example bone positioning guide that can be used with a multi-diameter fixation pin.

FIG. 6 illustrates an example bone positioning guide 10 that may be used as part of a surgical procedure involving a multi-diameter fixation pin 300. In this example a bone positioning guide 10 includes a main body member 20 and a shaft 30. The bone engagement member 40 is connected to the shaft and a tip 50 is connected to the main body member. In general, the main body member 20 can be sized and shaped to clear anatomy or other instrumentation (e.g., pins and guides) while positioned on a patient. Main body member 20 is illustrated as having a generally C-shaped configuration with a first end 60 and a second end 70.

Shaft 30 can be movably connected to the main body member 20 proximate its first end 60. In some embodiments, the shaft 30 includes threads 80 that engage with the main body member 20 such that rotation of the shaft translates the shaft with respect to the main body member. In other embodiments, the shaft can slide within the main body member and can be secured thereto at a desired location with a set screw. In yet other embodiments, the shaft can be moved with respect to the main body by a ratchet mechanism. In the embodiment shown, the shaft moves along an axis that intersects the tip 50.

Bone positioning guide 10 can include a bone engagement member 40 having a surface 90 configured to contact a bone, such as a metatarsal or a cuneiform. In the embodiment shown, the surface 90 is concave. Such a surface is adapted to promote surface contact with a generally cylindrical bone, such as a metatarsal. In use, bone engagement member 40 can be positioned in contact with a first bone portion (e.g., a first metatarsal) and tip can be positioned in contact with a second bone portion, such as an adjacent bone (e.g., second metatarsal or third metatarsal). Bone positioning guide 10 can include an actuator (e.g., a knob or a handle) 120 to actuate the positioning guide and move bone engagement member 40 relative to tip 50. In the embodiment shown, the actuator can be useful for allowing a user to rotate the shaft with respect to the main body member 20.

In some configurations, bone positioning guide 10 includes a cannulation 130, such as a cannulation 130 extending through the actuator, shaft, and bone engagement member. Multi-diameter fixation pin 300 can be placed through cannulation 130 and into contact with or through a bone engaged with the bone engagement member. For example, fixation wire 300 can be placed into the bone engaged with bone engagement member 40 to fix the position of the bone engagement member with respect to the bone. In another example, fixation wire 300 can be placed through the bone in contact with the bone engagement member and into an adjacent bone (e.g., second metatarsal) to maintain a bone position of the bone in contact with the bone engagement member and the adjacent bone. Fixation pin 300 can be inserted through cannulation 130 and into one or more bone portions using powered driver 318.

Figure 7:
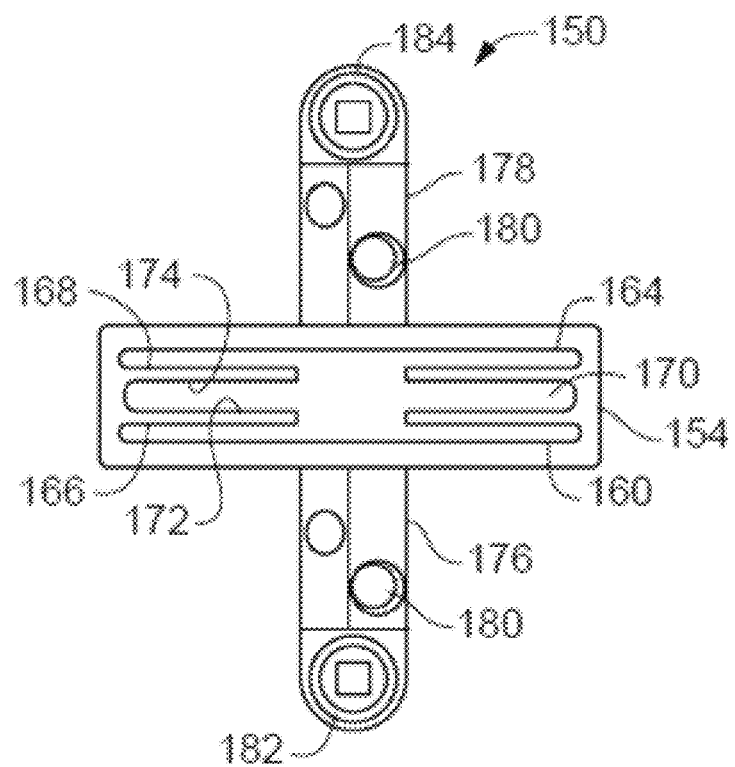
FIG. 7 is a top plan view of an example bone preparation guide that can be used with a multi-diameter fixation pin.

FIG. 7 illustrates an example bone preparation guide 150 that may be used as part of a surgical procedure involving a multi-diameter fixation pin 300. In some examples, bone preparation guide 150 includes a body 154 defining a first guide surface 160 to define a first preparing plane and a second guide surface 164 to define a second preparing plane. A tissue removing instrument (e.g., a saw, rotary bur, osteotome, etc., not shown) can be aligned with the surfaces to remove tissue (e.g., remove cartilage or bone and/or make cuts to bone). The first and second guide surfaces 160, 164 can be spaced from each other by a distance, (e.g., between about 2 millimeters and about 10 millimeters, such as between about 4 and about 7 millimeters). In the embodiment shown, the first and second guide surfaces are parallel, such that cuts to adjacent bones using the guide surfaces will be generally parallel.

In some configurations, as shown in FIG. 7, a first facing surface 166 is positioned adjacent the first guide surface 160 and/or a second facing surface 168 is positioned adjacent the second guide surface 164. In such configurations, the distance between the first guide surface and the first facing surface defines a first guide slot, and the distance between the second guide surface and the second facing surface defines a second guide slot. Each slot can be sized to receive a tissue removing instrument to prepare the bone ends. The first and second slots may be parallel or skewed. In the illustrated example, the facing surfaces each contain a gap, such that the surface is not a single, continuous surface. In other embodiments, the facing surfaces can be a single, continuous surface lacking any such gap.

An opening 170 can be defined by the body 154 between the first and second guide surfaces. The opening can be an area between the guide surfaces useful for allowing a practitioner to have a visual path to bones during bone preparation and/or to receive instruments. In the configuration shown, the opening extends across the body and a distance from a surface 172 opposite of the first facing surface 166 to a surface 174 opposite of the second facing surface 168.

The illustrated bone preparation guide also includes a first end 176 extending from the body 154 in a first direction and a second end 178 extending from the body in a second direction. The second direction can be different than the first direction (e.g., an opposite direction). As shown, each of the first end and the second end can include at least one fixation aperture 180 configured to receive a fixation pin to secure the bone preparation guide to an underlying bone. For example, first end 176 of bone preparation guide 150 may define a first fixation aperture through which a first pin is inserted and the second end 178 of bone preparation guide 150 may define a second fixation aperture through which a second pin is inserted. The first and second pins may be inserted using powered driver 318 and may have a constant diameter across their length. The first end 176 and/or the second end 178 of bone preparation guide 150 may also defined one or more additional fixation apertures that are angled (at a non-zero degree angle) or otherwise skewed relative to the two parallel fixation apertures.

In use, a clinician may insert the two pins (e.g., parallel pins) through fixation apertures 180 and may optionally insert one or more angled pins through the one or more angled fixation apertures. This combination of parallel and angled pins may prevent bone preparation guide 150 from being removed from the underlying bones being worked upon.

Figure 13:
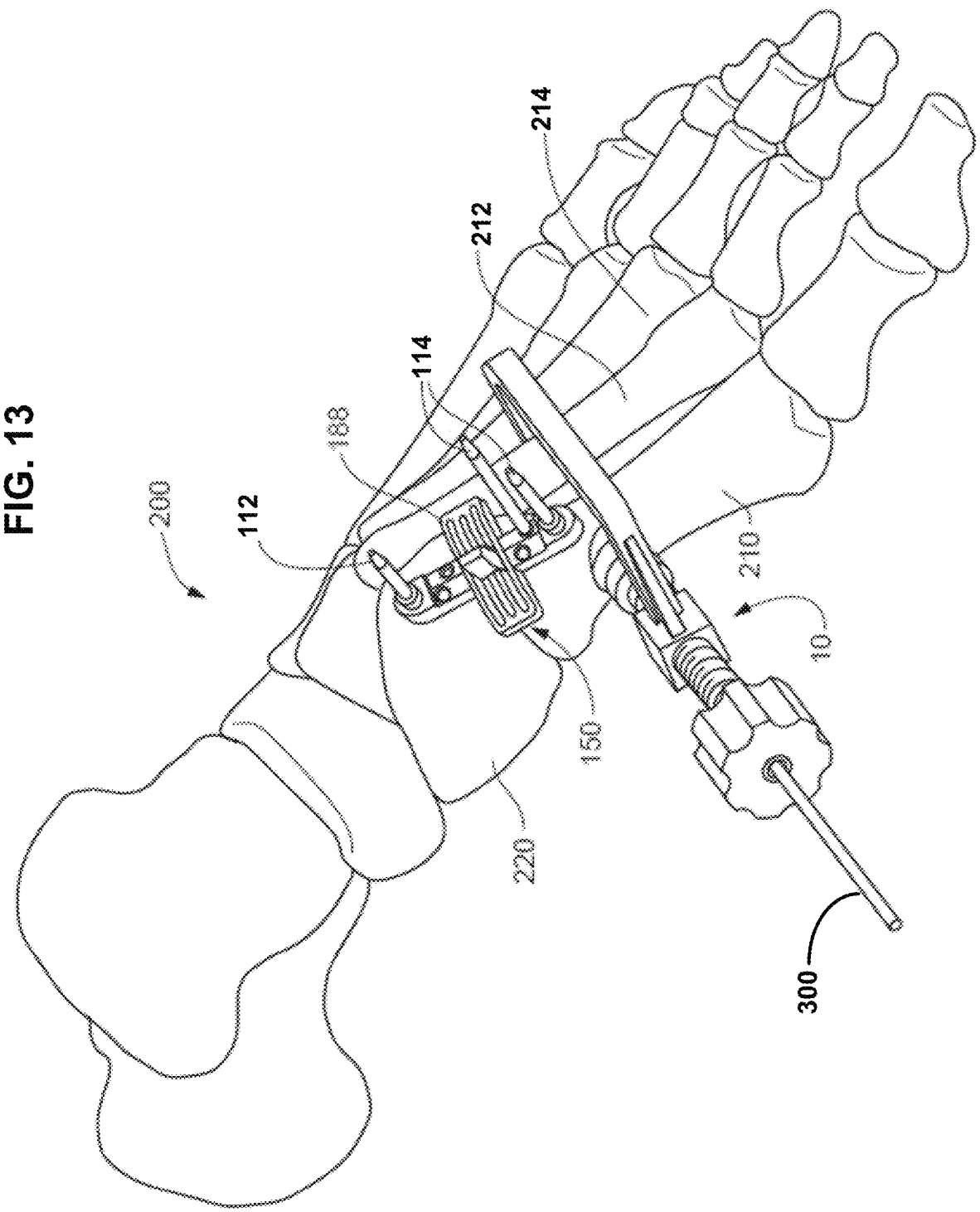
FIG. 13 is a perspective view of a foot depicting a bone preparation guide on the foot with pins inserted through the bone preparation guide.

In some examples as shown in FIG. 13, bone preparation guide 150 can also include a first adjustable stabilization member 182 engaged with the first end 176 and/or a second adjustable stabilization member 184 engaged with the second end 178. Each of the members can be threaded and engage a threaded aperture defined by the ends. The elevation of each end can be adjusted with respect to a bone by adjusting the stabilization member. In some embodiments, as shown, the stabilization members are cannulated such that they can receive a fixation pin.

Figure 8:
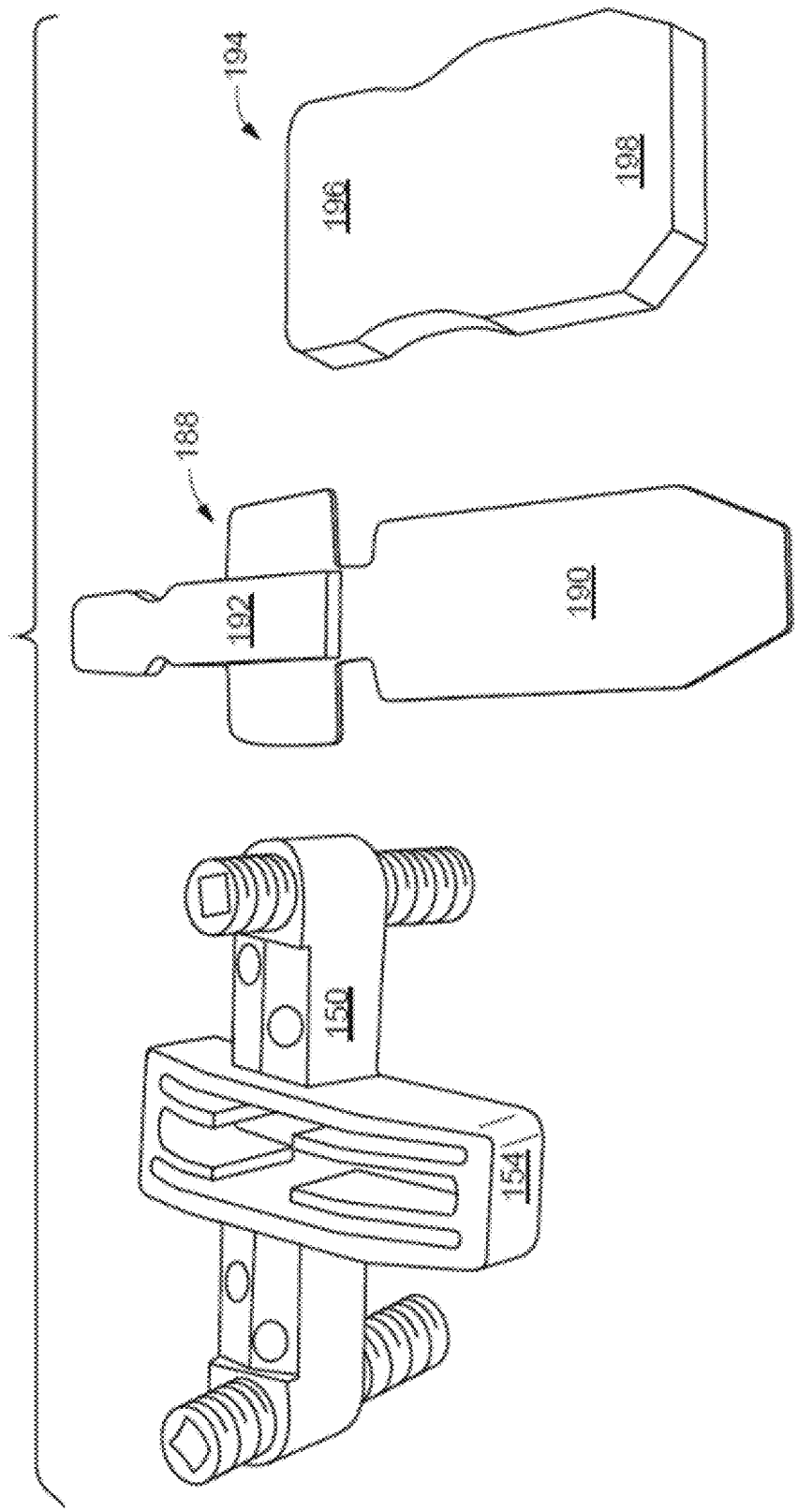
FIG. 8 is a perspective view of an example bone preparing guide, spacer, and tissue removing instrument check member that can be used with a multi-diameter fixation pin.

With reference to FIG. 8, bone preparation guide 150 may include or be used with a spacer 188 that extends downward from the body 154. Spacer 188 may be configured to be placed into a joint (e.g., within the TMT joint). In some embodiments, the spacer 188 is selectively engageable with the body of the bone preparation guide and removable therefrom. The spacer can have a first portion 190 configured to extend into a joint space and a second portion 192 engageable with the body 154. In the embodiment shown, the spacer can be received within opening 170, such that the spacer extends from the body in between the first and second guide surfaces. Such a spacer can be useful for positioning the body at a desired position with respect to a joint and for properly positioning the guide with respect to bones to be cut in more than one plane (e.g., three planes selected from more than one of a frontal plane, a transverse plane, and a sagittal plane). The distance between the spacer and the first guide surface can define a length of tissue removal (e.g., bone or cartilage to be cut) from a first bone, and the distance between the spacer and the second guide surface can define a length of tissue removal (e.g., bone or cartilage to be cut) from a second bone.

As also shown in FIG. 8, bone preparation guide 150 may include or be used with a tissue removal location check member 194. Tissue removal check member 194 may be engageable with the body 154 and configured to extend to a first bone and a second bone. The tissue removal location check member can have a first portion 196 configured to extend into contact with first and second bones and a second portion 198 engageable with the body. In the embodiment shown, the tissue removal check member 194 is configured to extend in the body 154 at both the first and second guiding surfaces. The tissue removal location check member 194 may be useful for allowing a practitioner to see where a tissue removing instrument guided by the surfaces will contact the bone to be prepared.

Bone preparation facilitated by bone preparation guide 150 can be useful, for instance, to facilitate contact between leading edges of adjacent bones, separated by a joint, or different portions of a single bone, separated by a fracture, such as in a bone alignment and/or fusion procedure. A bone may be prepared using one or more bone preparation techniques. In some applications, a bone is prepared by cutting the bone. The bone may be cut transversely to establish a new bone end facing an opposing bone portion. Additionally or alternatively, the bone may be prepared by morselizing an end of the bone. The bone end can be morselized using any suitable tool, such as a rotary bur, osteotome, or drill. The bone end may be morselized by masticating, fenestrating, crushing, pulping, and/or breaking the bone end into smaller bits to facilitate deformable contact with an opposing bone portion.

During a surgical technique utilizing fixation pin 300, a bone may be moved from an anatomically misaligned position to an anatomically aligned position with respect to another bone. Further, both the end of the moved bone and the facing end of an adjacent end may be prepared for fixation. In some applications, the end of at least one of the moved bone and/or the other bone is prepared after moving the bone into the aligned position. In other applications, the end of at least one of the moved bone and/or the other bone is prepared before moving the bone into the aligned position.

Movement of one bone relative to another bone can be accomplished using one or more instruments and/or techniques. In some examples, bone movement is accomplished using a bone positioning device that applies a force to one bone at a single location, such that the bone both translates and rotates in response to the force. This may be accomplished, for example, using a bone positioning guide that includes a bone engagement member, a tip, a mechanism to urge the bone engagement member and the tip towards each other, and an actuator to actuate the mechanism. Additionally or alternatively, bone movement may be accomplished using a compressor-distractor. As yet a further addition or alternative, a clinician may facilitate movement by physically grasping a bone, either through direct contact with the bone or indirectly (e.g., by inserting a K-wire such as fixation pin 300, grasping with a tenaculum, or the like), and moving his hand to move the bone.

An example method for preforming a bone alignment procedure utilizing a compressor-distractor and instrument defining a sliding surface according to the disclosure will now be described with respect to FIGS. 9-15 depicting a foot 200 having a first metatarsal 210, a medial cuneiform 222, and a second metatarsal 212. Unless otherwise indicated, the example steps described can be carried out in any order and need not be performed in the order described.

Figure 9:
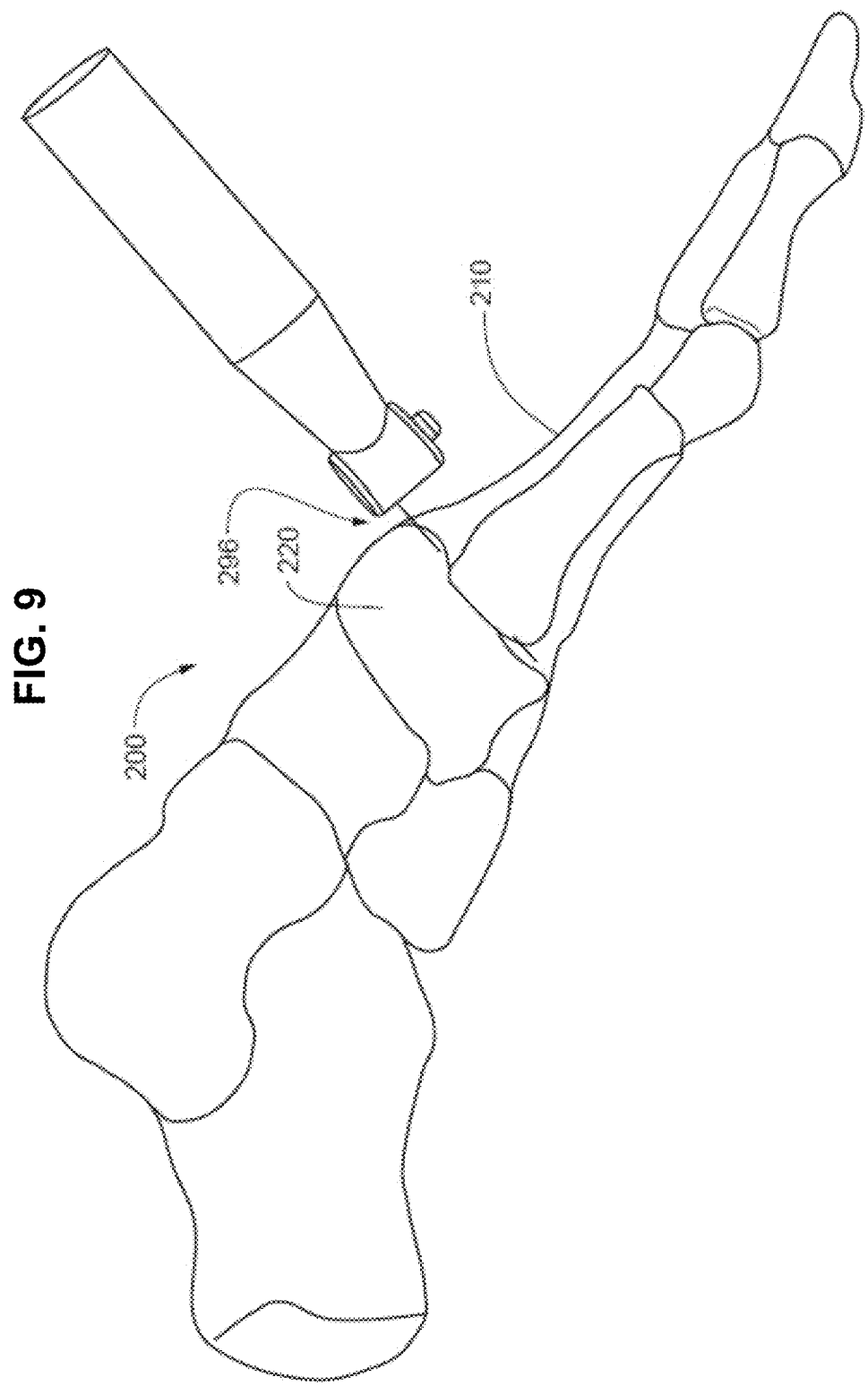
FIG. 9 is a perspective view of a foot depicting a bone positioning guide on the foot prior to an alignment of a first metatarsal.

After customary surgical preparation and access, a bone preparation instrument 296 can be inserted into the joint (e.g., first tarsal-metatarsal joint) to release soft tissues and/or excise the plantar flare from the base of the first metatarsal 210, as shown in FIG. 9. Excising the plantar flare may involve cutting plantar flare off the first metatarsal 210 so the face of the first metatarsal is generally planar. This step helps to mobilize the joint to facilitate a deformity correction. In some embodiments, the dorsal-lateral flare of the first metatarsal may also be excised to create space for the deformity correction (e.g., with respect to rotation of the first metatarsal). In certain embodiments, a portion of the metatarsal base facing the medial cuneiform can be removed during this mobilizing step.

Figure 10:
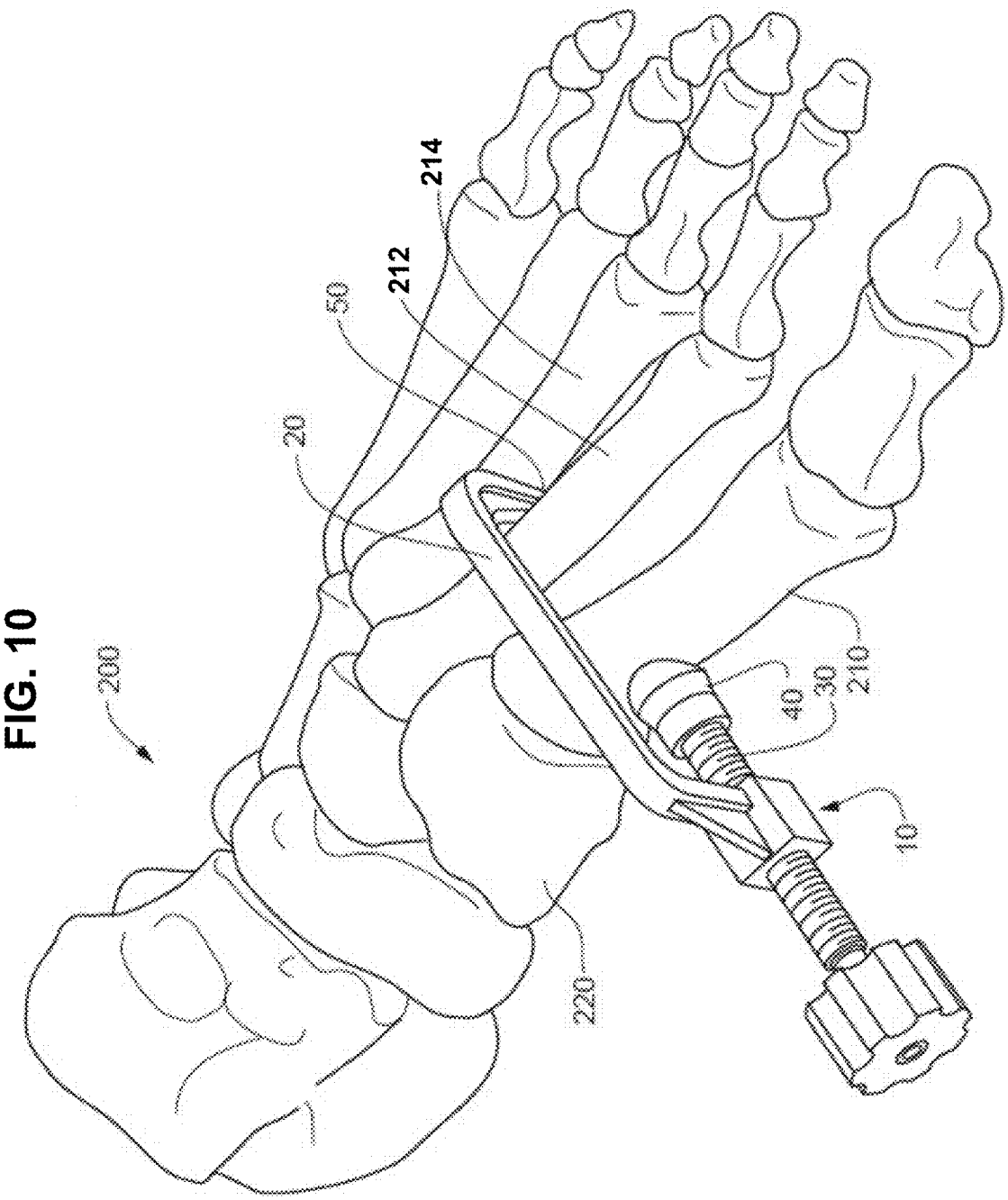
FIG. 10 is a perspective view of a foot depicting a bone positioning guide on the foot.

An incision can be made and, if a bone positioning instrument is going to be used, a tip 50 of a bone positioning guide 10 inserted on the lateral side of a metatarsal other than the first metatarsal 210, such as the second metatarsal 212. As shown in FIG. 10, the tip can be positioned proximally at a base of the second metatarsal 212 and a third metatarsal 294 interface. A surface of a bone engagement member 40 can be placed on the proximal portion of the first metatarsal 210. In some embodiments, the bone engagement member engages a medial ridge of the first metatarsal 210. As shown, the body 20 of the positioning guide can be generally perpendicular to the long axis of the second metatarsal 212.

To help avoid a base shift, a clinician can insert a fulcrum in the notch between first metatarsal 210 and second metatarsal 212 at the base of the metatarsals (e.g., adjacent respective cuneiform) before actuating bone positioning guide 10 or otherwise moving the first metatarsal relative to the medial cuneiform. The fulcrum can provide a point about which first metatarsal 210 can rotate and/or pivot while helping minimize or avoid base compression between the first metatarsal and the second metatarsal.

In applications utilizing bone positioning guide 10, the actuator on the bone positioning guide can be actuated to reduce the angle (transverse plane angle between the first metatarsal and the second metatarsal) and rotate the first metatarsal about its axis (frontal plane axial rotation). The first metatarsal 210 can be properly positioned with respect to the medial cuneiform 222 by moving the bone engagement member 40 bone positioning guide with respect to the tip 50 of the bone positioning guide. In some embodiments, such movement simultaneously pivots the first metatarsal with respect to the cuneiform and rotates the first metatarsal about its longitudinal axis into an anatomically correct position to correct a transverse plane deformity and a frontal plane deformity. Other instrumented and/or non-instrumented approaches can be used to adjustment position of first metatarsal 210 relative to medial cuneiform 222. Thus, other applications utilizing compressor-distractor 100 and a pin lock may be performed without utilizing bone positioning guide 10.

Figure 11:
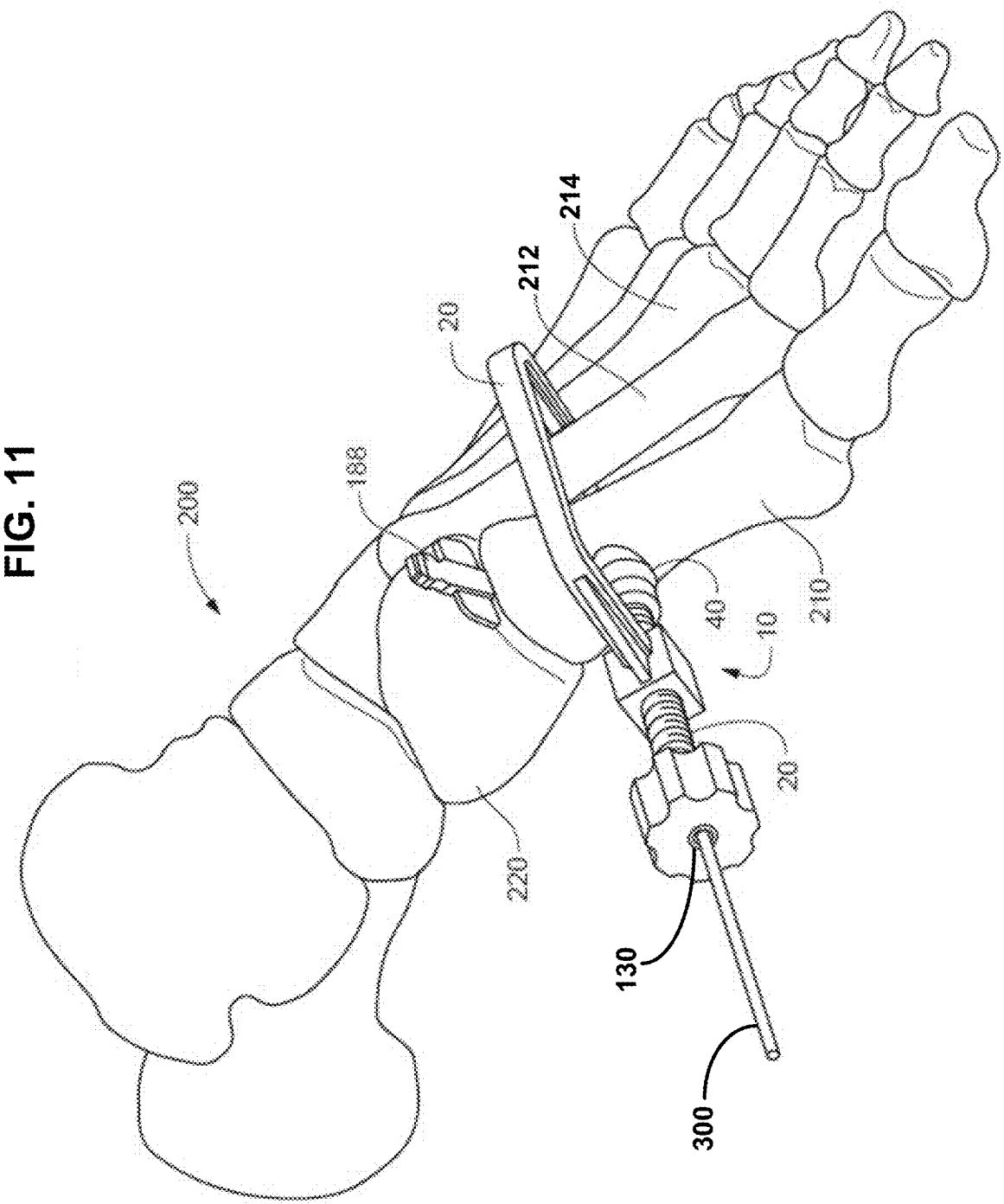
FIG. 11 is a perspective view of a foot depicting a bone positioning guide on the foot after an alignment of a first metatarsal and with a spacer inserted into a joint space.

Independent of whether bone positioning guide 10 is used, an example technique may include inserting fixation pin 300 into and through first metatarsal 210 into an adjacent bone, such as second metatarsal 212 and/or medial cuneiform 220. The clinician may insert driver engagement portion 306 of fixation pin 300 into powered driver 318 and use the driver to drive the bone insertion portion of the pin into first metatarsal 210. The clinician may drive bone insertion portion 308 through cannulation 130, through first metatarsal 210, and into second metatarsal 212, as illustrated in FIG. 11. The clinician may detach powered driver 318, leaving fixation pin 300 in the bones to temporarily fixate the moved position of the first metatarsal.

Figure 12:
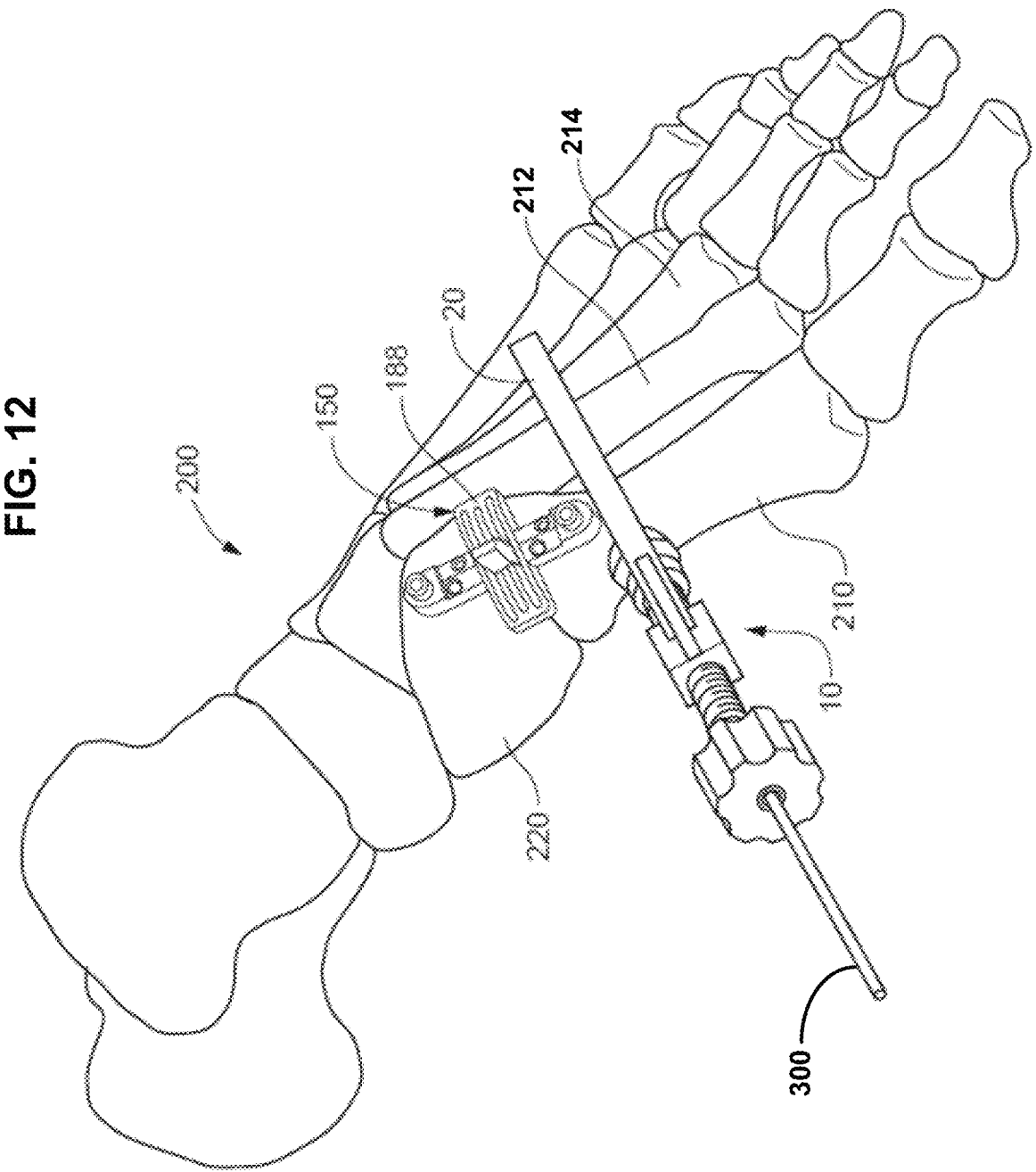
FIG. 12 is a perspective view of a foot depicting a bone preparation guide positioned on the foot.

As also illustrated in FIG. 11, the example technique may involve positioning joint spacer 188 within the joint between first metatarsal 210 and medial cuneiform 222. Bone preparation guide 150 can be placed over the joint spacer 188 as shown in FIG. 12 and engaged with the joint spacer to set a position and orientation of the bone preparation guide relative to the joint. In other embodiments, bone preparation guide 150 is placed on the bones without using joint spacer 188 to aid with positioning.

As depicted in FIG. 13, one or more fixation pins can be inserted into apertures of the bone preparation guide 150 to secure the guide to the first metatarsal 210 and the medial cuneiform 222. The fixation pins inserted into the apertures of bone preparation guide 150 includes a first fixation pin 112 and second fixation pin 114. The first and second fixation pins may or may not be multi-diameter fixation pins. For example, the first and second fixation pins may have a constant diameter across their length. The clinician may insert first and second fixation pins 112, 114 using the same driver 318 and same collet 320 used to insert fixation pin 300. One or more additional pins can be inserted at an angle or in a converging orientation to help prevent movement of the bone preparation guide 150 during a tissue removing step. After insertion of the pins, the spacer 188 (if used) can optionally be removed in embodiments having a selectively engageable spacer.

In some applications, the end of the first metatarsal 210 facing the medial cuneiform 222 can be prepared with a tissue removing instrument 296 guided by a guide surface of bone preparation guide 150 (e.g., inserted through a slot defined by a first guide surface and a first facing surface). In some embodiments, the first metatarsal 210 end preparation is done after at least partially aligning the bones, e.g., by actuating bone positioning guide 10 or otherwise moving the first metatarsal but after preparing the end of first metatarsal 210. In other embodiments, the first metatarsal 210 end preparation is done before the alignment of the bones.

In addition to preparing the end of first metatarsal 210, the end of the medial cuneiform 222 facing the first metatarsal 210 can be prepared with the tissue removing instrument 296 guided by a guide surface of bone preparation guide 150 (e.g., inserted through a slot defined by a second guide surface and a second facing surface). In some embodiments, the medial cuneiform 222 end preparation is done after the alignment of the bones. In yet other embodiments, the medial cuneiform 222 end preparation is done before the alignment of the bones. In embodiments that include cutting bone or cartilage, the cuneiform cut and the metatarsal cut can be parallel, conforming cuts. In some examples, a saw blade can be inserted through a first slot to cut a portion of the medial cuneiform and the saw blade can be inserted through a second slot to cut a portion of the first metatarsal.

Figure 14:
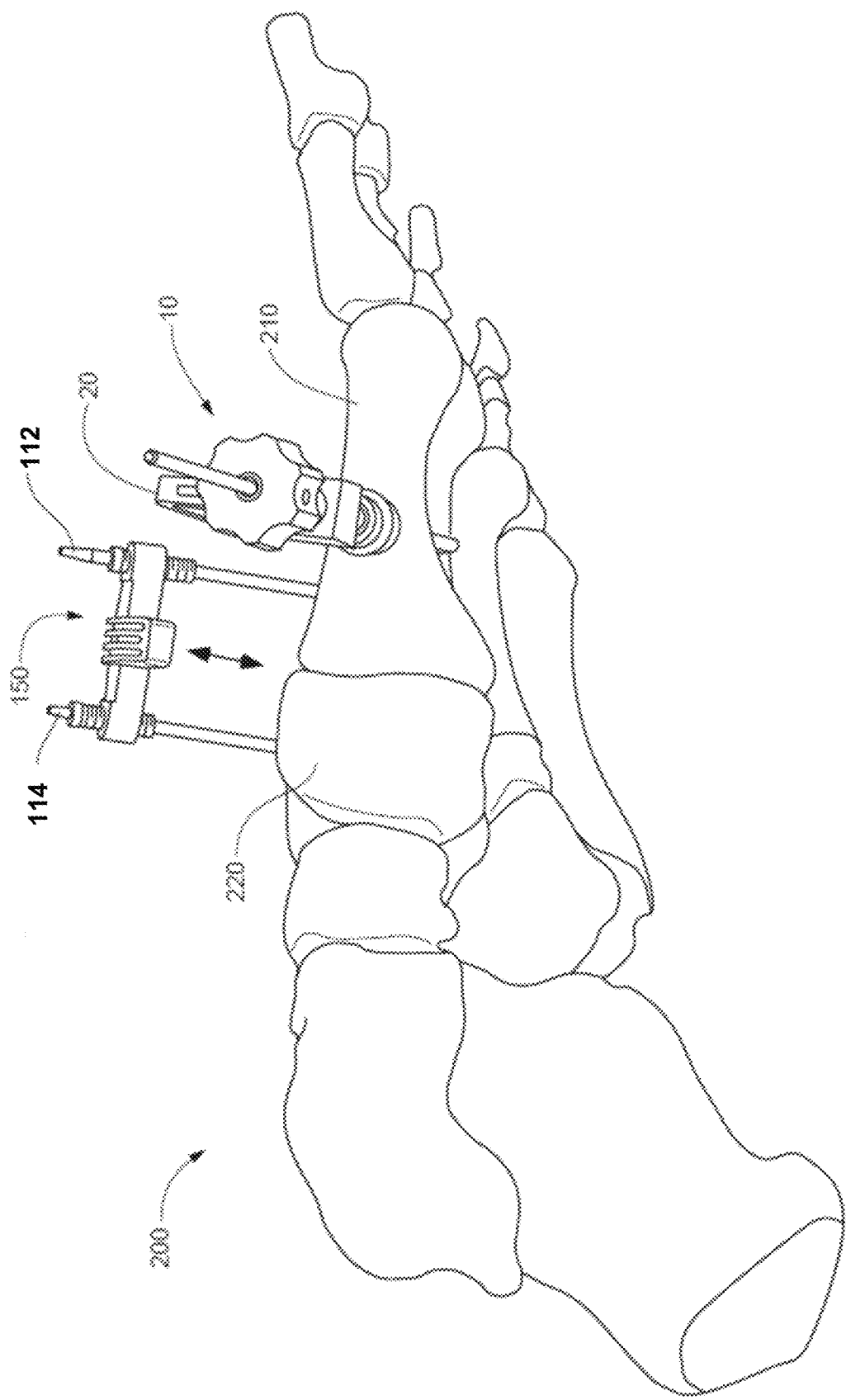
FIG. 14 is a perspective view of a foot depicting a removal of a bone preparation guide.
Figure 15:
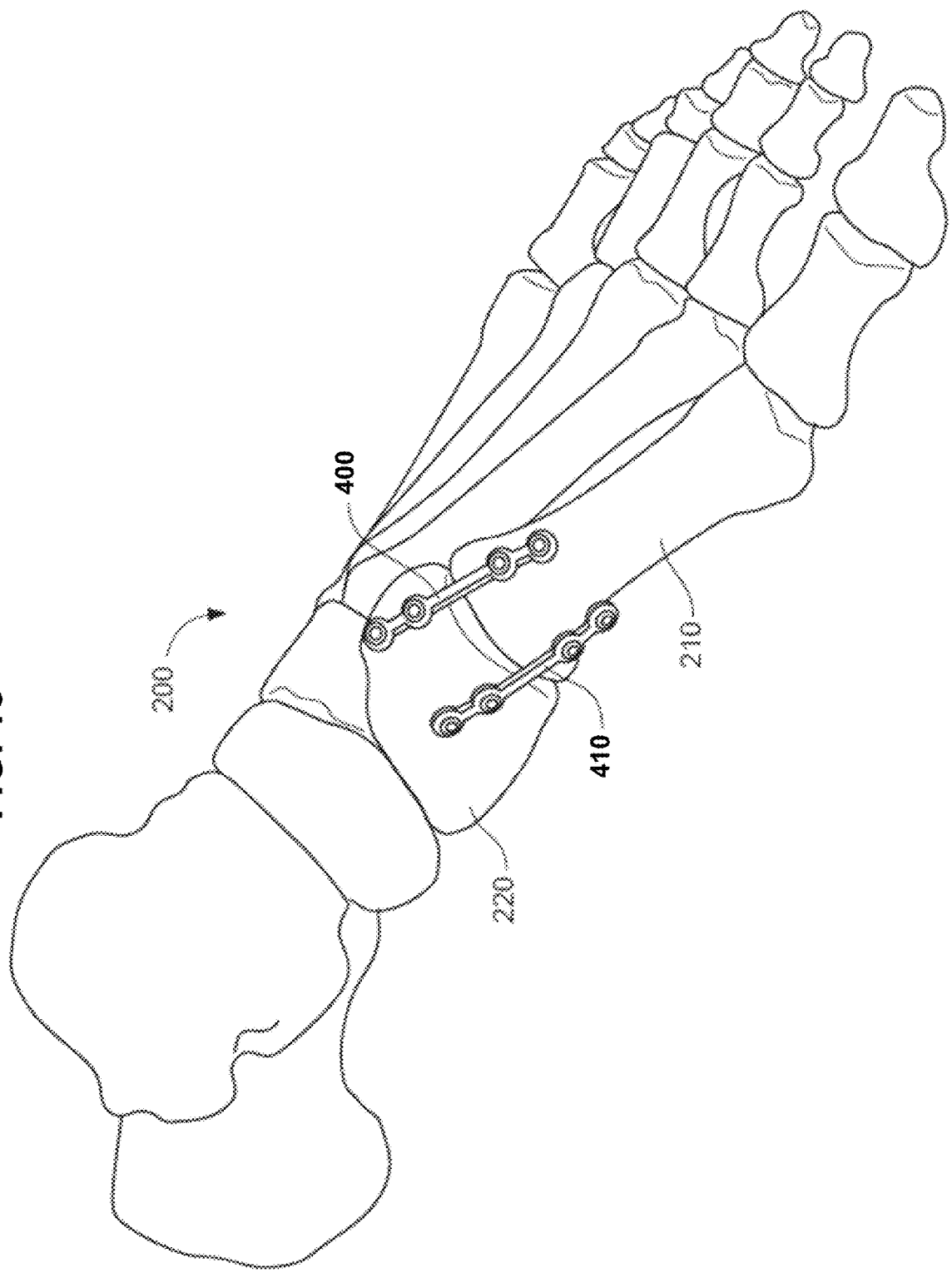
FIG. 15 is a side perspective view of a foot depicting bone plates across a joint between first and second bones.

Any angled/converging pins can be removed and the bone preparation guide 150 can be lifted off the substantially parallel first and second pins 112, 114, as shown in FIG. 14. In applications where bone positioning guide 10 is utilized, the bone positioning guide may be removed before or after bone preparation guide 150 is removed. In either case, in some examples, a temporary fixation pin 300 may be used to maintain the position of the underlying bones (e.g., first metatarsal 210 relative to medial cuneiform 222) while bone preparation guide 150 is removed and compressor-distractor 100 is installed.

With the end faces of the metatarsal and cuneiform optionally pressed together via a compressor-distractor, the clinician may provisionally or permanently fixate the bones or bones portions together. For example, one or more bone fixation devices can be applied across the joint and to the two bones to stabilize the joint for fusion, such as two bone plates positioned in different planes. FIG. 14 illustrates an example fixation device arrangement that includes a first bone plate 400 positioned on a dorsal-medial side of the first metatarsal and medial cuneiform and a second bone plate 410 positioned on a medial-plantar side of the first metatarsal and the medial cuneiform. In other embodiments, second bone plate 410 can be a helical bone plate positioned from a medial side of the cuneiform to a plantar side of the first metatarsal across the joint space. The plates can be applied with the insertion of bone screws. Example bone plates that can be used as first bone plate 400 and/or second bone plate 410 are described in US Patent Publication No. US2016/0192970, titled "Bone Plating System and Method" and filed Jan. 7, 2016, which is incorporated herein by reference. Other types in configurations of bone fixation devices can be used, and the disclosure is not limited in this respect. Any temporary fixation pins 300 inserted into the bones can be removed once permanent fixation is applied.

Multi-diameter fixation pins, along with associated techniques and systems, have been described. In some examples, a multi-diameter fixation pin according to the disclosure is included in a disposable, sterile kit that includes associated surgical instrumentation, such as bone positioning guide and/or a preparation guide described herein. Other components that may be included within the sterile kit include bone fixation devices, bone fixation screws, single diameter pins for insertion into pin-receiving holes, and the like.

Various examples have been described. These and other examples are within the scope of the following claims.

The invention claimed is:

1. A method comprising:
inserting a pin having a first diameter into a collet of a powered driver and driving the pin into at least one of a metatarsal and a cuneiform;
moving the metatarsal relative to the cuneiform to establish a moved position of the metatarsal;
inserting a driver engagement portion of a multi-diameter fixation pin into the collet of the powered driver and driving a bone insertion portion of the multi-diameter fixation pin through the metatarsal and into another bone to hold the moved position of the metatarsal,
wherein the collet of the powered driver is sized to receive the pin having the first diameter and the driver engagement portion of the multi-diameter fixation pin but not the bone insertion portion of the multi-diameter fixation pin.

2. The method of claim 1, wherein inserting the pin having the first diameter into the collet of the powered driver and driving the pin into at least one of the metatarsal and the cuneiform comprises:
inserting a first pin having the first diameter into the collet of the powered driver and driving the pin into one of the metatarsal and the cuneiform,
removing the first pin from the collet of the powered driver while the first pin remains in the one of the metatarsal and cuneiform,
inserting a second pin having the first diameter into the collet of the powered driver and driving the pin into the other of the metatarsal and the cuneiform, and
removing the second pin from the collet of the powered driver while the second pin remains in the other of the metatarsal and cuneiform.

3. The method of claim 1, wherein inserting the driver engagement portion of the multi-diameter fixation pin into the collet of the powered driver comprises inserting the multi-diameter fixation pin into the collet to a depth less than or equal to a depth denoted by an indicator on the multi-diameter fixation pin.

4. The method of claim 3, wherein the indicator comprises a notch formed into a perimeter surface of the multi-diameter fixation pin.

5. The method of claim 1, wherein the first diameter and a diameter of the driver engagement portion each ranges from 2.0 mm to 3.2 mm, and a diameter of the bone insertion portion ranges from 0.7 mm to 1.8 mm.

6. The method of claim 1, wherein the first diameter and a diameter of the driver engagement portion each are greater than or equal to 2.0 mm, and a diameter of the bone insertion portion is less than 2.0 mm.

7. The method of claim 1, wherein driving the bone insertion portion of the multi-diameter fixation pin through the metatarsal into another bone comprises driving the bone insertion portion of the multi-diameter fixation pin through the metatarsal into an adjacent metatarsal.

8. The method of claim 1, wherein driving the pin having the first diameter into at least one of a metatarsal and a cuneiform comprises:
driving a first pin having the first diameter into the metatarsal,
driving a second pin having the first diameter into the cuneiform, and
attaching a bone preparation guide to the metatarsal via the first pin and to the cuneiform via the second pin.

9. The method of claim 8, wherein the bone preparation guide comprises a body with a first guide surface to define a first preparing plane and a second guide surface to define a second preparing plane, the first guide surface being positioned over the metatarsal, and the second guide surface being positioned over the cuneiform.

10. The method of claim 8, further comprising preparing an end of the metatarsal through the bone preparation guide and preparing an end of the cuneiform through the bone preparation guide.

11. The method of claim 1, wherein the metatarsal is a first metatarsal and the cuneiform is a medial cuneiform.

12. The method of claim 1, wherein:
the multi-diameter fixation pin defines a body extending from a first end to a second end opposite the first end,
the body defines the driver engagement portion having the first diameter and the bone insertion portion having a second diameter less than the first diameter; and
the first end of the body defines a tip.

13. The method of claim 12, wherein the body further defines a taper portion between the driver engagement portion and the bone insertion portion, the taper portion having a diameter that transitions from the first diameter to the second diameter.

14. The method of claim 12, wherein the body is a unitary unity body formed of a single piece material.

15. A method comprising:
inserting a driver engagement portion of a multi-diameter fixation pin into a collet of a powered driver and driving a bone insertion portion of the multi-diameter fixation pin through at least one bone portion,
wherein the collet of the powered driver is sized to receive the driver engagement portion of the multi-diameter fixation pin but not the bone insertion portion of the multi-diameter fixation pin.

16. The method of claim 15, wherein inserting the driver engagement portion of the multi-diameter fixation pin into the collet of the powered driver comprises inserting the multi-diameter fixation pin into the collet to a depth less than or equal to a depth denoted by an indicator on the multi-diameter fixation pin.

17. The method of claim 16, wherein the indicator comprises a notch formed into a perimeter surface of the multi-diameter fixation pin.

18. The method of claim 15, wherein a diameter of the driver engagement portion ranges from 2.0 mm to 3.2 mm, and a diameter of the bone insertion portion ranges from 0.7 mm to 1.8 mm.

19. The method of claim 15, wherein:
the multi-diameter fixation pin defines a body extending from a first end to a second end opposite the first end, the body defines the driver engagement portion having a first diameter and the bone insertion portion having a second diameter less than the first diameter; and
the first end of the body defines a tip configured for insertion into the at least one bone portion.

20. The method of claim 19, wherein the body further defines a taper portion between the driver engagement portion and the bone insertion portion, the taper portion having a diameter that transitions from the first diameter to the second diameter.

* * * * *